(12) United States Patent
Willis

(10) Patent No.: US 7,610,078 B2
(45) Date of Patent: Oct. 27, 2009

(54) SYSTEM AND METHOD OF GRAPHICALLY GENERATING ANATOMICAL STRUCTURES USING ULTRASOUND ECHO INFORMATION

(75) Inventor: N. Parker Willis, Atherton, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 804 days.

(21) Appl. No.: 11/213,516

(22) Filed: Aug. 26, 2005

(65) Prior Publication Data

US 2007/0049821 A1 Mar. 1, 2007

(51) Int. Cl.
*A61B 5/05* (2006.01)
(52) U.S. Cl. .................. 600/424; 600/443; 382/154
(58) Field of Classification Search .............. 382/128, 382/154; 600/374, 424, 443, 459; 700/98, 700/118; 345/419, 420, 424
See application file for complete search history.

(56) References Cited

U.S. PATENT DOCUMENTS

| | | | |
|---|---|---|---|
| 5,383,874 A | 1/1995 | Jackson et al. | |
| 5,391,199 A | 2/1995 | Ben-Haim | |
| 5,485,849 A | 1/1996 | Panescu et al. | |
| 5,494,042 A | 2/1996 | Panescu et al. | |
| 5,833,621 A | 11/1998 | Panescu et al. | |
| 5,941,825 A | 8/1999 | Lang et al. | |
| 5,983,126 A | 11/1999 | Wittkampf | |
| 6,019,725 A | 2/2000 | Vesely et al. | |
| 6,101,409 A | 8/2000 | Swanson et al. | |
| 6,216,027 B1 | 4/2001 | Willis et al. | |
| 6,235,024 B1 | 5/2001 | Tu | |
| 6,490,474 B1 | 12/2002 | Willis et al. | |
| 6,546,276 B1 | 4/2003 | Zanelli | |
| 6,716,166 B2 | 4/2004 | Govari | |
| 6,716,174 B1 | 4/2004 | Li | |
| 6,719,700 B1 | 4/2004 | Willis | |
| 6,751,492 B2 | 6/2004 | Ben-Haim | |
| 6,773,402 B2 * | 8/2004 | Govari et al. ............... 600/459 |
| 6,824,515 B2 | 11/2004 | Suorsa et al. | |
| 6,896,657 B2 | 5/2005 | Willis | |
| 6,950,689 B1 | 9/2005 | Willis et al. | |
| 2003/0078494 A1 | 4/2003 | Panescu et al. | |

(Continued)

OTHER PUBLICATIONS

Office Action dated Jun. 13, 2008 for U.S. Appl. No. 11/213,020, filed Aug. 26, 2005, inventor: N. Parker Willis (9 pages).

*Primary Examiner*—Long V Le
*Assistant Examiner*—Saurel J Selkin
(74) *Attorney, Agent, or Firm*—Vista IP Law Group LLP

(57) ABSTRACT

Methods and systems for graphically creating a representation of an anatomical structure, such as a heart, is provided. The distal end of an elongated probe is moved within the anatomical structure, and geometric shapes are defined within a coordinate system. By defining geometric shapes, such as spheres or circles, as the distal probe end is moved within the anatomical structure, the cavity within the anatomical structure can be represented. A representation of at least a portion of the anatomical structure can be graphically generated based on the geometric shapes, e.g., by determining a union of the geometric shapes and conforming the graphical representation around the union of the shapes. In the case of a heart, the union of the shapes will generally represent the blood volume within the heart, so that the graphical anatomical representation (which in this case will be a graphical representation of the endocardial surface of the heart) can be accurately conformed around the representative blood volume.

52 Claims, 15 Drawing Sheets

U.S. PATENT DOCUMENTS

| | | |
|---|---|---|
| 2005/0080334 A1 | 4/2005 | Willis |
| 2005/0090744 A1 | 4/2005 | Willis |
| 2005/0203375 A1 | 9/2005 | Willis et al. |
| 2005/0261580 A1 | 11/2005 | Willis et al. |

* cited by examiner

RECEIVE

| TRANSMIT | TXVR1 | TXVR2 | TXVR3 | TXVR4 | TXVR5 | TXVR6 | TXVR7 | TXVR8 | RX1 | RX2 | RX3 | TXVR9 | TXVR10 | TXVR11 |
|---|---|---|---|---|---|---|---|---|---|---|---|---|---|---|
| TXVR1 | ✗ | $t_1$ | $t_2$ | $t_3$ | $t_4$ | $t_5$ | $t_6$ | $t_7$ | $t_8$ | $t_9$ | $t_{10}$ | ✗ | ✗ | ✗ |
| TXVR2 | $t_{11}$ | ✗ | $t_{12}$ | $t_{13}$ | $t_{14}$ | $t_{15}$ | $t_{16}$ | $t_{17}$ | $t_{18}$ | $t_{19}$ | $t_{20}$ | ✗ | ✗ | ✗ |
| TXVR3 | $t_{21}$ | $t_{22}$ | ✗ | $t_{23}$ | $t_{24}$ | $t_{25}$ | $t_{26}$ | $t_{27}$ | $t_{28}$ | $t_{29}$ | $t_{30}$ | ✗ | ✗ | ✗ |
| TXVR4 | $t_{31}$ | $t_{32}$ | $t_{33}$ | ✗ | $t_{34}$ | $t_{35}$ | $t_{36}$ | $t_{37}$ | $t_{38}$ | $t_{39}$ | $t_{40}$ | ✗ | ✗ | ✗ |
| TXVR5 | $t_{41}$ | $t_{42}$ | $t_{43}$ | $t_{44}$ | ✗ | $t_{45}$ | $t_{46}$ | $t_{47}$ | $t_{48}$ | $t_{49}$ | $t_{50}$ | ✗ | ✗ | ✗ |
| TXVR6 | $t_{51}$ | $t_{52}$ | $t_{53}$ | $t_{54}$ | $t_{55}$ | ✗ | $t_{56}$ | $t_{57}$ | $t_{58}$ | $t_{59}$ | $t_{60}$ | ✗ | ✗ | ✗ |
| TXVR7 | $t_{61}$ | $t_{62}$ | $t_{63}$ | $t_{64}$ | $t_{65}$ | $t_{66}$ | ✗ | $t_{67}$ | $t_{68}$ | $t_{69}$ | $t_{70}$ | ✗ | ✗ | ✗ |
| TXVR8 | $t_{71}$ | $t_{72}$ | $t_{73}$ | $t_{74}$ | $t_{75}$ | $t_{76}$ | $t_{77}$ | ✗ | $t_{78}$ | $t_{79}$ | $t_{80}$ | ✗ | ✗ | ✗ |
| TXVR9 | ✗ | ✗ | ✗ | ✗ | ✗ | ✗ | ✗ | ✗ | ✗ | ✗ | ✗ | $t_{81}$ | ✗ | ✗ |
| TXVR10 | ✗ | ✗ | ✗ | ✗ | ✗ | ✗ | ✗ | ✗ | ✗ | ✗ | ✗ | ✗ | $t_{82}$ | ✗ |
| TXVR11 | ✗ | ✗ | ✗ | ✗ | ✗ | ✗ | ✗ | ✗ | ✗ | ✗ | ✗ | ✗ | ✗ | $t_{83}$ |

*FIG. 7*

RECEIVE

| TRANSMIT | TXVR1 | TXVR2 | TXVR3 | TXVR4 | TXVR5 | TXVR6 | TXVR7 | TXVR8 | RX1 | RX2 | RX3 | TXVR9 | TXVR10 | TXVR11 |
|---|---|---|---|---|---|---|---|---|---|---|---|---|---|---|
| TXVR1 | ✗ | $t_1$ | $t_2$ | $t_3$ | $t_4$ | $t_5$ | $t_6$ | $t_7$ | $t_8$ | $t_9$ | $t_{10}$ | ✗ | ✗ | ✗ |
| TXVR2 | $t_{11}$ | ✗ | $t_{12}$ | $t_{13}$ | $t_{14}$ | $t_{15}$ | $t_{16}$ | $t_{17}$ | $t_{18}$ | $t_{19}$ | $t_{20}$ | ✗ | ✗ | ✗ |
| TXVR3 | $t_{21}$ | $t_{22}$ | ✗ | $t_{23}$ | $t_{24}$ | $t_{25}$ | $t_{26}$ | $t_{27}$ | $t_{28}$ | $t_{29}$ | $t_{30}$ | ✗ | ✗ | ✗ |
| TXVR4 | $t_{31}$ | $t_{32}$ | $t_{33}$ | ✗ | $t_{34}$ | $t_{35}$ | $t_{36}$ | $t_{37}$ | $t_{38}$ | $t_{39}$ | $t_{40}$ | ✗ | ✗ | ✗ |
| TXVR5 | $t_{41}$ | $t_{42}$ | $t_{43}$ | $t_{44}$ | ✗ | $t_{45}$ | $t_{46}$ | $t_{47}$ | $t_{48}$ | $t_{49}$ | $t_{50}$ | ✗ | ✗ | ✗ |
| TXVR6 | $t_{51}$ | $t_{52}$ | $t_{53}$ | $t_{54}$ | $t_{55}$ | ✗ | $t_{56}$ | $t_{57}$ | $t_{58}$ | $t_{59}$ | $t_{60}$ | ✗ | ✗ | ✗ |
| TXVR7 | $t_{61}$ | $t_{62}$ | $t_{63}$ | $t_{64}$ | $t_{65}$ | $t_{66}$ | ✗ | $t_{67}$ | $t_{68}$ | $t_{69}$ | $t_{70}$ | ✗ | ✗ | ✗ |
| TXVR8 | $t_{71}$ | $t_{72}$ | $t_{73}$ | $t_{74}$ | $t_{75}$ | $t_{76}$ | $t_{77}$ | ✗ | $t_{78}$ | $t_{79}$ | $t_{80}$ | ✗ | ✗ | ✗ |
| TXVR9 | ✗ | ✗ | ✗ | ✗ | ✗ | ✗ | ✗ | ✗ | ✗ | ✗ | ✗ | $t_{81a,b}$ | ✗ | ✗ |
| TXVR10 | ✗ | ✗ | ✗ | ✗ | ✗ | ✗ | ✗ | ✗ | ✗ | ✗ | ✗ | ✗ | $t_{82a,b}$ | ✗ |
| TXVR11 | ✗ | ✗ | ✗ | ✗ | ✗ | ✗ | ✗ | ✗ | ✗ | ✗ | ✗ | ✗ | ✗ | $t_{83a,b}$ |

*FIG. 8*

SYSTEM AND METHOD OF GRAPHICALLY GENERATING ANATOMICAL STRUCTURES USING ULTRASOUND ECHO INFORMATION

FIELD OF THE INVENTION

The present inventions generally relate to medical probes, and more particularly to systems and methods for navigating medical probes within anatomical organs or other anatomical structures.

BACKGROUND OF THE INVENTION

It is often necessary or desirable to determine the location of a medical probe relative to a location of interest within three-dimensional space. In many procedures, such as interventional cardiac electrophysiology therapy, it is important for the physician to know the location of a probe, such as a catheter, (especially, a therapeutic catheter) relative to the patient's internal anatomy. During these procedures, a physician, e.g., steers an electrophysiology (EP) mapping catheter through a main vein or artery into the interior region of the heart that is to be treated. The physician then determines the source of the cardiac rhythm disturbance (i.e., the targeted cardiac tissue) by placing mapping elements carried by the catheter into contact with the heart tissue, and operating the mapping catheter to generate an EP map of the interior region of the heart. Having identified the targeted cardiac tissue, the physician then steers an ablation catheter (which may or may not be the same catheter as the mapping catheter above) into the heart and places an ablating element carried by the catheter tip near the targeted cardiac tissue, and directs energy from the ablating element to ablate the tissue and form a lesion, thereby treating the cardiac disturbance.

Traditionally, navigation of catheters relative to points of interest has been accomplished using fluoroscopy. In this case, radiopaque elements are located on the distal end of the catheter and fluoroscopically imaged as the catheter is routed through the body. As a result, a two-dimensional image of the catheter, as represented by the illuminated radiopaque elements, is generated, thereby allowing the physician to roughly determine the location of the catheter. The use of fluoroscopy in locating catheters is somewhat limited, however, in that the physician is only able to visualize the catheter and surrounding tissues in two dimensions. In addition, fluoroscopy does not image soft tissues, making it difficult for the physician to visualize features of the anatomy as a reference for the navigation. Thus, fluoroscopy is sub-optimal for the purpose of navigating a catheter relative to anatomical structure composed primarily of soft tissues, e.g., within the heart.

Various types of three-dimensional medical systems (e.g., the Realtime Position Management™ (RPM) tracking system, developed commercially by Boston Scientific Corporation and described in U.S. Pat. No. 6,216,027 and U.S. patent application Ser. No. 09/128,304, entitled "A Dynamically Alterable Three-Dimensional Graphical Model of a Body Region," and the CARTO EP Medical system, developed commercially by Biosense Webster and described in U.S. Pat. No. 5,391,199) have been developed, or at least conceived, to address this issue. In these medical systems, a graphical representation of the catheter or a portion thereof is displayed in a three-dimensional computer-generated representation of a body tissue, e.g., a heart chamber. The three-dimensional representation of the body tissue is produced by mapping the geometry of the inner surface of the body tissue in a three-dimensional coordinate system, e.g., by moving a mapping device to multiple points on the body tissue. The position of the device to be guided within the body tissue is determined by placing one or more tracking elements on the device and tracking the position of these elements within the three-dimensional coordinate system.

In the RPM tracking system, this is accomplished by moving the mapping device within the heart chamber to acquire a volume of interior anatomical points (i.e., points within the blood pool) and deforming a graphical anatomical surface to be coincident with the outermost interior anatomical points as each anatomical point is acquired. The anatomical surface can be made more accurate by touching the endocardial surface with the mapping device to acquire anatomical surface points and tying the anatomical surface to these points. In the CARTO EP medical system, a multitude of anatomical surface points are acquired, and once a sufficient number is acquired, a graphical anatomical surface is created based on the surface points.

In both of the RPM and CARTO EP systems, once the graphical heart representation has been created, an EP mapping catheter, which includes at least one tracking element, so that it can be tracked within the three-dimensional coordinate system, is used to acquire EP information along the endocardial surface. An electrical activity map can then be generated from the acquired EP information and superimposed over the graphical heart representation. An ablation catheter, which like the EP mapping catheter, includes at least one tracking element, so that it can be tracked within the three-dimensional coordinate system, is placed into contact with the targeted treatment regions identified in the electrical activity map and operated to therapeutically ablate the tissue.

While the RPM and CARTO EP systems have generally been successful in providing a means for navigating catheters within anatomical structures, the anatomical information acquired by the mapping device at any given moment is represented by a single point. As such, many anatomical measurements must be made to create a relatively accurate graphical reconstruction of the anatomical structure, thereby increasing the time required to perform the relevant medical procedure. In addition, when creating anatomical surface points, the accuracy of the resulting graphical model will depend upon whether or not contact between the mapping device and the surface of the anatomical structure has actually been made during acquisition of the surface points. However, it is difficult to ensure that such contact is always made, thereby resulting in some inaccuracies within the graphical model. It is also sometimes difficult to determine when the EP mapping catheter and ablation catheter are in contact with the endocardial surface during the EP mapping and ablation functions, thereby making the medical procedure more tedious.

There thus remains a need for an improved system and method for generating graphical representations of anatomical structures and navigating medical devices within such anatomical structures.

SUMMARY OF THE INVENTION

In accordance with an aspect of the present inventions, a method of graphically creating a representation of an anatomical structure is provided. The method comprises moving the distal end of an elongated probe within the anatomical structure (such as, e.g., a heart), and defining geometric shapes within a coordinate system (such as, e.g., a three-dimensional coordinate system) while the distal probe end is moved within the anatomical structure. In one exemplary method, the geometric shapes comprises three-dimensional shapes, such as spheres, and/or two-dimensional shapes, such as circles. The size of each geometric shape can be determined by a distance between the distal probe end and a surface of the anatomical structure, which in one method, can be determined by transmitting a signal, such as an ultrasound signal, from the probe distal end, wherein the distance can be determined based on an intersection between the signal and the surface of the anatomical structure. The position of each geometric shape in the coordinate system can be determined by transmitting ranging signals between the probe distal end and a reference point, wherein a position of each geometric shape within the coordinate system is determined based on the ranging signals. By defining geometric shapes as the distal probe end is moved within the anatomical structure, the cavity within the anatomical structure can be represented.

The method further comprises graphically generating a representation of at least a portion of the anatomical structure based on the geometric shapes, e.g., by determining a union of the geometric shapes and conforming the graphical representation around the union of the shapes. In the case of a heart, the union of the shapes will generally represent the blood volume within the heart, so that the graphical anatomical representation (which in this case will be a graphical representation of the endocardial surface of the heart) can be accurately conformed around the representative blood volume. While the present inventions should not be limited in their broadest aspects, the use of shapes, as opposed to points, or even lines, provides more information from which the graphical generation of the anatomical structure is based. As such, the efficiency and/or accuracy of the graphical anatomical representation is generally increased. The geometric shapes can comprise different shapes and/or originate from a plurality of points on the probe to further increase the efficiency and/or accuracy of the graphical anatomical representation.

In accordance with another aspect of the present inventions, a medical system for use with an anatomical structure, such as a heart, is provided. The system comprises an elongated medical probe (such as, e.g., an intravascular catheter) including a shaft having a distal end and a signal emitting element (such as, e.g., an ultrasound transducer) carried by the shaft distal end. The system further comprises at least one processor configured for defining a plurality of geometric shapes within a coordinate system based on the signal emitted by the element. As discussed above, the coordinate system can be a three-dimensional coordinate system and the geometric shapes may comprise three-dimensional shapes, such as spheres, and/or two-dimensional shapes, such as circles. The processor(s) is further configured for graphically generating a representation of at least a portion of the anatomical structure based on the geometric shapes, e.g., by determining the union of the geometric shapes and generating the graphical representation based on the union. The system may optionally comprise an output device, such as a monitor, for displaying the graphical anatomical representation.

In one embodiment, the medical probe includes a plurality of signal emitting elements carried by the distal shaft end, in which case, the processor(s) may be configured for defining the geometric shapes based on the signals emitted by the elements. In another embodiment, the element is configured for emitting signal in at least two different modes, so that at least two different geometric shapes can be respectively defining based on the at least two modes, thereby increasing the efficiency and/or accuracy of the graphical anatomical representation.

In one embodiment, the size of each geometric shape is defined by a distance between the distal shaft end and a surface of the anatomical structure, in which case, the processor(s) can be configured for determining the distance based on an intersection between the emitted signal and the surface of the anatomical structure. The system may further comprise a tracking element (which may be the same as or collocated with the signal emitting element) carried by the distal shaft end, and ranging circuitry configured for transmitting signals between the tracking element and a reference point, wherein the processor(s) is configured for determining a position of each geometric shape within the coordinate system based on the signals.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 7 is a table illustrating a time matrix formed by calculating the times-of-flight of ultrasound signals transmitted between tracking elements and reference elements, and round trip time-of-flight of ultrasound signals transmitted between proximity elements and a tissue surface;

FIG. 8 is a table illustrating a time matrix formed by calculating the times-of-flight of ultrasound signals transmitted between tracking elements and reference elements, and round trip time-of-flight of ultrasound signals transmitted between proximity elements and a tissue surface when the proximity elements are operated in two vibration modes;

DETAILED DESCRIPTION OF THE PREFERRED EMBODIMENTS

Figure 1:
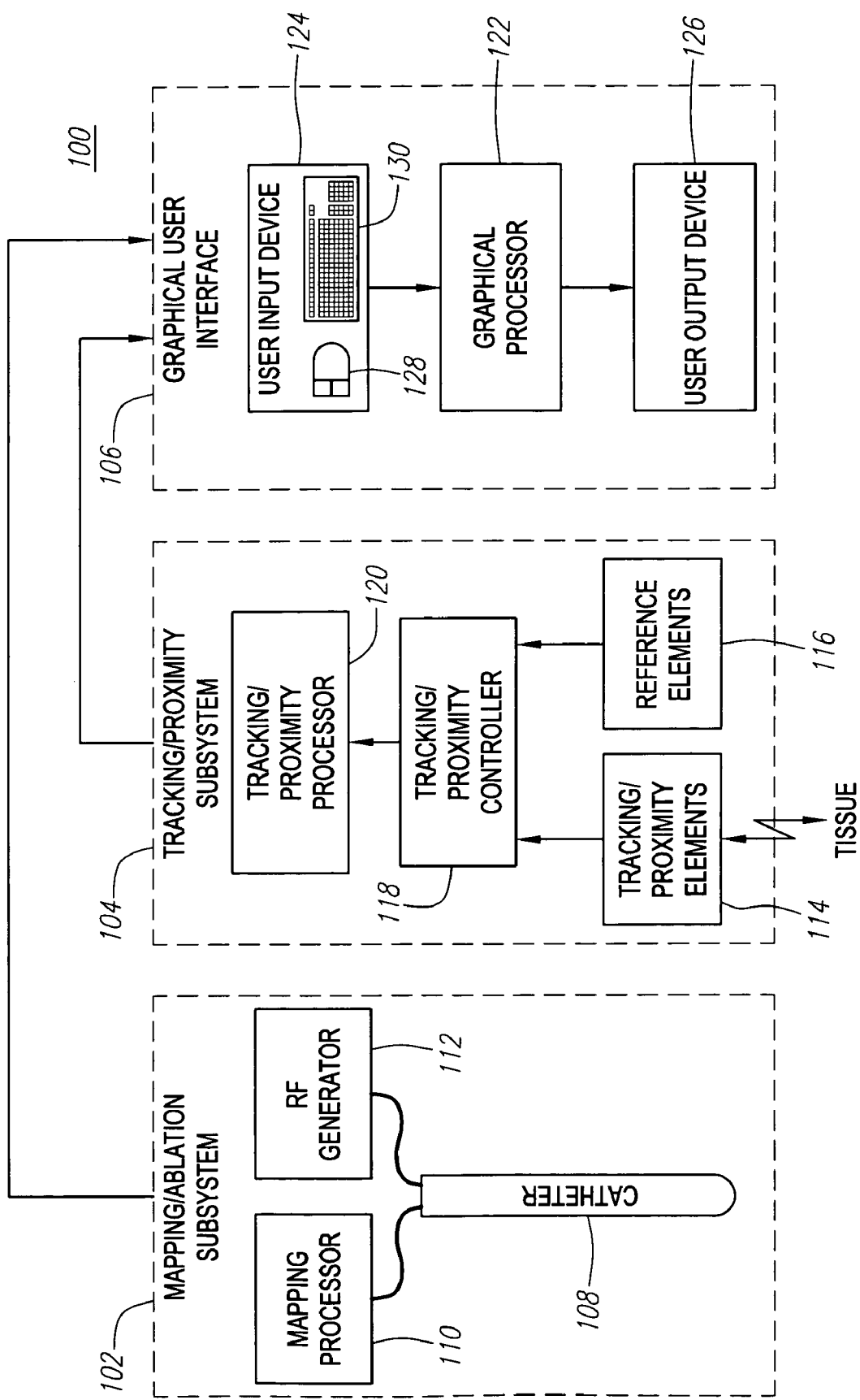
FIG. 1 is a functional block diagram of one preferred embodiment of a medical system constructed in accordance with the present inventions.

Referring to FIG. 1, an exemplary medical system 100 constructed in accordance with the present invention will be described. The medical system 100 is particularly suited for mapping and treating a heart with catheters. Nevertheless, it should be appreciated that similar types of medical systems can be used for treating, diagnosing, or otherwise graphically reconstructing other internal hollow anatomical structures, and can be used with medical devices other than catheters. The medical system 100 generally comprises (1) a mapping/ablation subsystem 102 for mapping and ablating tissue within the heart; (2) a tracking/proximity subsystem 104 for generating and receiving ranging signals used to measure distances within the heart; and (3) a graphical user interface 106 configured for generating and displaying graphics of the heart, electrical activity information, and medical devices within a three-dimensional coordinate system based on the ultrasound ranging signals. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Mapping/Ablation Subsystem

The mapping/ablation subsystem 102 is configured to identify and treat target tissue sites, e.g., aberrant conductive pathways. To this end, the mapping/ablation subsystem 102 comprises a mapping/ablation catheter 108, a mapping processor 110, and a radio frequency (RF) generator 112.

Figure 2:
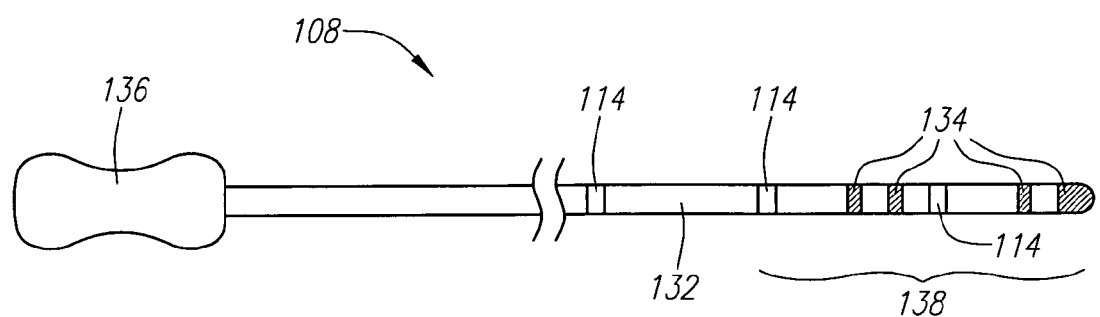
FIG. 2 is a plan view of a mapping/ablation catheter used in the medical system of FIG. 1.

As illustrated in FIG. 2, the mapping/ablation catheter 108 comprises an elongate catheter shaft 132, a plurality of electrodes 134 (in this case, four) carried at the distal end of the catheter shaft 114, and a handle 136 carried at the proximal end of the elongate shaft 114. All four electrodes 134 on the catheter shaft 132 are configured to detect electrical signals in the myocardial tissue of the heart for subsequent identification of target sites. The electrode 134 at the distal tip of the catheter shaft 132 is also configured to be used as an ablation electrode to provide ablation energy to the targeted sites when placed adjacent thereto and operated. The handle 136 includes an electrical connector (not shown) for electrical coupling to the mapping processor 110 and RF generator 112.

The distal end of the catheter shaft 132 comprises a rigid or semi-rigid straight section 138 that assumes a preshaped and known geometry in the absence of an external force. In particular, the pre-shaped catheter section 138 of the catheter shaft 132, although somewhat flexible when being navigated through the vasculature leading to the heart, maintains the preshaped geometry when navigated within the chambers of the heart and associated anatomical structures, such as the heart valves and vessel ostia.

Referring back to FIG. 1, the mapping processor 110 is configured to derive activation times and voltage distribution from the electrical signals obtained from the electrodes 134 to determine irregular electrical signals within the heart, which can then be graphically displayed as a map. Mapping of tissue within the heart is well known in the art, and thus for purposes of brevity, the mapping processor 110 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 112 is configured to deliver ablation energy to the ablation electrode (i.e., the distal most electrode 134) in a controlled manner in order to ablate sites identified by the mapping processor 110. Alternatively, other types of ablative sources besides the RF generator 112 can be used, e.g., a microwave generator, an acoustic generator, a cryoablation generator, and a laser or other optical generator. Ablation of tissue within the heart is well known in the art, and thus for purposes of brevity, the RF generator 112 will not be described in further detail. Further details regarding RF generators are provided in U.S. Pat. No. 5,383,874, which is expressly incorporated herein by reference.

It should be noted that other types of mapping/ablation catheters can be used in the medical system 100. For example, a catheter having a basket structure of resilient splines, each of which carries a plurality of dedicated mapping electrodes can be used. This catheter may be placed in a heart chamber, so that the resilient splines conform to the endocardial surface of the heart, thereby placing and distributing the mapping electrodes along the entire endocardial surface of the cavity for efficient mapping. The catheter may also have a roving ablation electrode that can be steered in contact with the ablation sites identified by the mapping electrodes. Or a separate ablation catheter with a dedicated ablation electrode or electrodes can be used. It should be noted that if the mapping/ablation catheter does have a basket structure that does not lend itself well to roving within the chambers of the heart, a separate roving catheter is preferably used to enable reconstruction of the heart.

II. Tracking/Proximity Subsystem

Referring still to FIG. 1, the tracking/proximity subsystem 104 performs tracking and proximity functions that ultimately allow determination of the locations of the catheter 108, the acquired electrical activity information, and the endocardial surface of the heart within a three-dimensional coordinate system. To this end, the tracking/proximity subsystem 104 includes (1) a plurality of elements 114, which function both as tracking elements and proximity elements; (2) a plurality of reference elements 116; (3) a controller 126 for coordinating the transmission of signals between the tracking/proximity elements 114 and reference elements 116 when performing a tracking function, and coordinating the transmission of signals between the tracking/proximity elements 114 and tissue when performing a proximity function; and (4) a processor 128 for determining the positional coordinates (x, y, z) of the tracking/proximity elements 114 within the three-dimensional coordinate system based on the transmitted signals between the tracking/proximity elements 114 and reference elements 116, and for determining the proximity between the tracking/proximity elements 114 and a location on the endocardial surface of the heart based on the transmitted signals between the tracking/proximity elements 114 and tissue.

Figure 3:
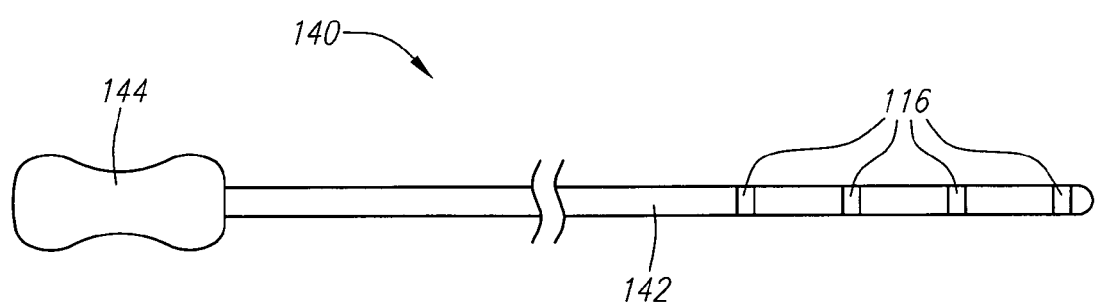
FIG. 3 is a plan view of a reference catheter used in the medical system of FIG. 1.

As shown in FIG. 2, the tracking/proximity elements 114 (in this case, three) are physically carried by the distal end of the mapping/ablation catheter 108. It should be noted that although the tracking/proximity elements 114 are carried by the mapping/ablation catheter 108, alternatively, the tracking/proximity elements 114 may be located on a separate device, such as a roving catheter, e.g., if the mapping/ablation catheter takes the form of a basket structure. As shown in FIG. 3, the reference elements 116 (in this case, four) are carried by a reference catheter 140. Like the mapping/ablation catheter 108, the reference catheter 140 comprises an elongate catheter shaft 142 and a handle 144 carried at the proximal end of the elongate shaft 142. The distal end of the reference catheter 140 may optionally comprise a plurality of electrodes (not shown), e.g., to provide the reference catheter 140 with mapping functionality. The reference catheter 140 can be placed anywhere within the body (preferably, a known location) that arranges the reference elements 116 in three-dimensional space, and that allows the reference elements 116 to communicate with the tracking elements 114. As will be described in further detail below, two of the reference catheters 140 are used for the tracking function.

In the illustrated embodiment, the tracking/proximity subsystem 104 is ultrasound-based, and thus, the tracking/proximity elements 114 and reference elements 116 take the form of ultrasound transducers, which are well-suited for serving as transmitters, receivers, or both. That is, ultrasound transducers can be operated as transmitters by stimulating them with electrical signals, which, in turn, causes the transducers to vibrate and transmit ultrasound signals. The ultrasound transducers can be operated as receivers by stimulating them with ultrasound signals, which, in turn, causes the transducers to vibrate and transmit electrical signals.

It should be noted that the tracking/proximity subsystem 104 can be based on signal types other than ultrasound. For example, magnetic tracking techniques, such as that disclosed in U.S. Pat. No. 5,391,199, which is expressly incorporated herein by reference, can be employed. As another example, a voltage tracking technique, such as that disclosed in U.S. Pat. No. 5,983,126, which is expressly incorporated herein by reference, can be employed. However, because the tracking/proximity elements 114 are additionally used for determining proximity to a tissue surface, which can be more efficiently performed using ultrasound, an ultrasound-based tracking/proximity subsystem 104 is preferred.

When performing a tracking function, the controller 126 is configured for transmitting signals between the tracking/proximity elements 114 and reference elements 116, so that the positional coordinates of the tracking/proximity elements 114, which will be physically associated with the catheter 108, can be determined within a three-dimensional coordinate system. To this end, the controller 126 operates the tracking/proximity elements 114 as receivers and the reference elements 116 as transceivers (i.e., the reference elements 116 have the capability of transmitting and receiving ultrasound signals). In particular, the controller 126 is operated to sequentially transmit ultrasound signals in the form of pulses (e.g., 500 KHz pulses) from each reference element 116 to the tracking/proximity elements 114 and remaining reference elements 116, while calculating the "time-of-flight" of the ultrasound signal between each pair of elements.

That is, when an electrical signal is applied to the transmitting element by the controller 126, the transmitting element vibrates at an associated resonant frequency. When the transmitting element is in fluid, such as blood, this causes an ultrasound signal to propagate away from the transmitting element. When the wavefront of the ultrasound signal encounters the receiving element, it converts the ultrasound signal back into an electrical signal. Thus, the controller 126 can calculate the "time-of-flight" of the ultrasound signal between the elements based on the elapsed time between the transmission of the ultrasound signal and the receipt of the ultrasound signal. Note that, in performing the tracking function, no transducer transmits to itself, and thus, the first wavefront of the ultrasound signal received by each transducer can be assumed to be unreflected, and thus, will accurately represent the distance between the transmitting and receiving transducers.

When performing a proximity function, the controller 126 is configured for transmitting signals from the tracking/proximity elements 114 to the endocardial surface, and for receiving the reflected signals from the endocardial surface, so that the minimum distance between known positions in the three-dimensional coordinate system and the endocardial surface can be determined. To this end, the controller 126 operates each tracking/proximity element 114 as a transceiver by transmitting ultrasound signals in the form of pulses (e.g., a 500 KHz pulses) from the respective tracking/proximity element 114 to the endocardial surface, where it is reflected and received back at the same tracking/proximity element 114. The controller 126 calculates the fastest "round trip time-of-flight" of the ultrasound signal from the respective tracking/proximity element 114 to the closest endocardial surface, and back to the same tracking/proximity element 114.

That is, when an electrical signal is applied to the tracking/proximity element 114 by the controller 126, the tracking/proximity element 114 vibrates at an associated resonant frequency. When the tracking/proximity element 114 is in fluid, such as blood, this causes an ultrasound pulse to propagate away from the tracking/proximity element 114. When the wavefront of the ultrasound signal encounters the endocardial surface or any other mechanical discontinuity, a certain percentage of the ultrasound signal reflects off of the tissue. The amount of the reflected signal and the directions in which the signal is reflected is a function of the characteristics of the blood/tissue interface, the frequency of ultrasound, the surface geometry of the tissue, the angle of incidence, and a number of other factors. In any case, a portion of the reflected ultrasound signal will be directed back towards the tracking/proximity element 114, which converts the ultrasound signal back into an electrical signal. Thus, the controller 126 can calculate the "round-trip time-of-flight" of the ultrasound signal based on the elapsed time between the transmission of the ultrasound signal and the receipt of the reflected ultrasound signal.

It should be noted that although the elements 114 function as both tracking and proximity elements, separate tracking elements and proximity elements can be used. However, because it is preferred to provide the proximity of the endocardial surface in relation to a known positional coordinate within the three-dimensional coordinate, it is advantageous to utilize, as the proximity element, a tracking element, the coordinates of which will be known. Also, less than all of the elements 114 can be used as a proximity element. For example, in an alternative embodiment, only the distal-most element 114 may function as both a tracking element and proximity element.

Figure 4:
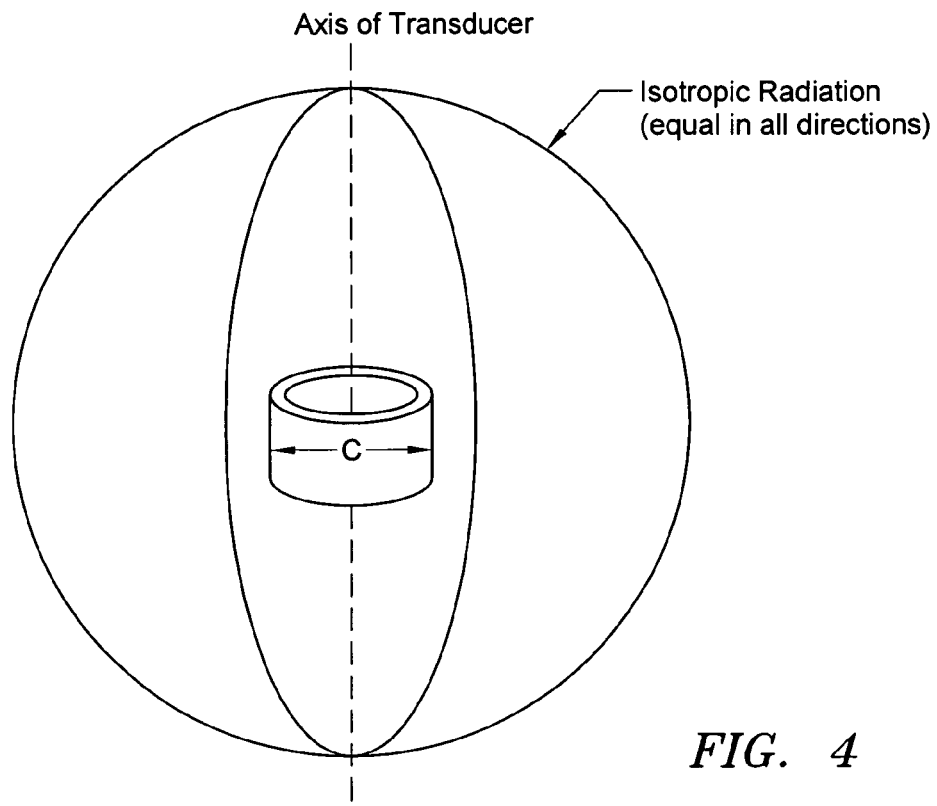
FIG. 4 is a perspective view of a cylindrical ring transducer operated in a circumferential vibration mode to transmit and/or receive isotropic ultrasound signals in the medical system of FIG. 1.
Figure 5:
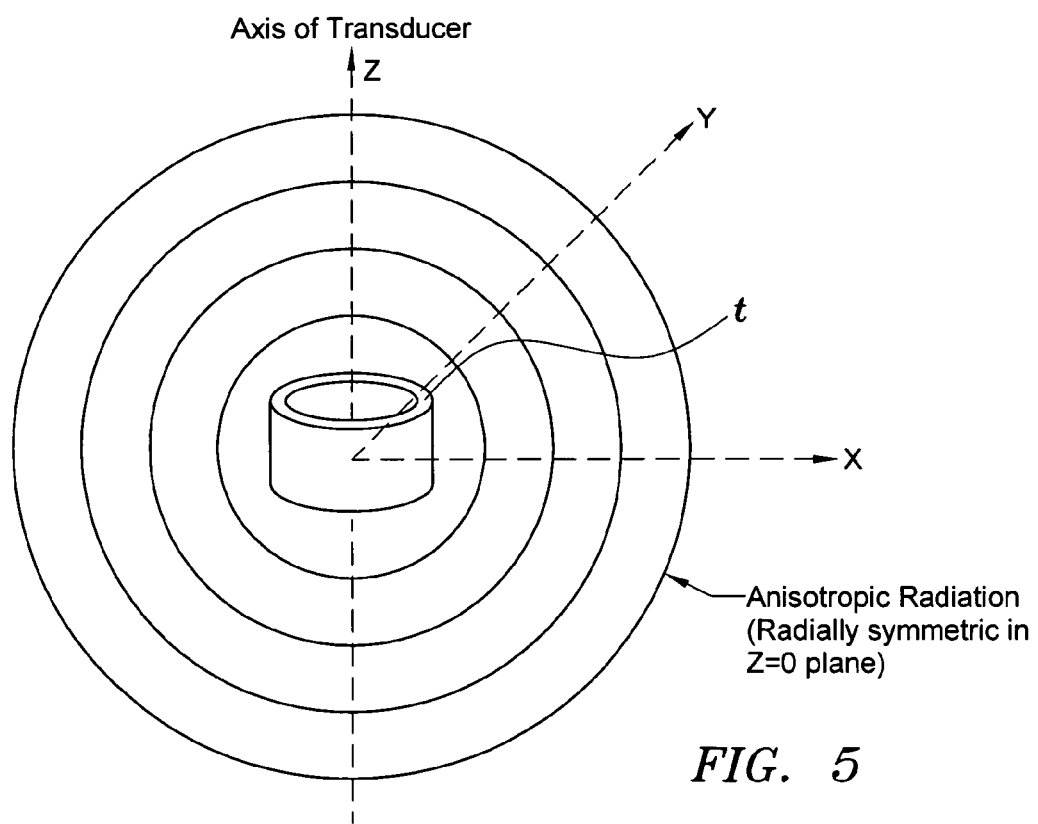
FIG. 5 is a perspective view of a cylindrical ring transducer operated in a thickness vibration mode to transmit and/or receive anisotropic ultrasound signals in the medical system of FIG. 1.

It should be noted that ultrasound transducers may be advantageously operated in several modes. In particular, the vibration of an ultrasound transducer results from the piezoelectric ceramic expanding in one direction, which causes it to contract in another direction. Each direction of expansion/contraction is termed a vibrational mode. Each vibration mode of a transducer is associated with a resonant frequency (i.e., the frequency of expansion/contraction), which is determined by the size and geometry of the transducer, and the speed of sound in the piezoelectric ceramic. In the illustrated embodiment, cylindrical ring transducers, such as those illustrated in FIGS. 4 and 5 are used. For the purposes of the invention, a ring transducer exhibits two vibrational modes that can be utilized in the system 100.

The first mode is the circumferential mode, which is caused by expansion/contraction along the circumference c of the transducer, and results in the emission or reception of an ultrasound signal in a generally isotropic fashion (FIG. 4). That is, the ultrasound signal transmitted or received by the transducer has a beam profile that is substantially equal in all directions. The second mode is the thickness mode, which is caused by expansion/contraction along the thickness t of the transducer, and results in the transmission and reception of an ultrasound signal in an anisotropic fashion (FIG. 5). That is, each of the ultrasound signals transmitted or received by the transducer has a beam profile that exhibits low points or nulls. In this case, the beam profile radiates in a radially symmetric manner along a plane perpendicular to the axis of the ring transducer. The circumferential and thickness modes of the ring transducer can be generated by stimulating the transducer at the two respective resonant frequencies. Both modes can be simultaneously generated by stimulating the transducer with an electrical pulse having a relatively short width that spreads the harmonic frequencies over a broad range that includes the resonant frequencies.

When performing the tracking function, the circumferential mode, which is much more isotropic than the thickness mode, is used, so that any receiving transducer spaced from the transmitting transducer will receive the transmitted ultrasound signal in a manner that provides a consistent "time-of flight" measurement between two transducers, regardless of the transducer orientations. It should be noted, however, that because the discontinuities between the different surfaces of the ultrasound transducer create discontinuities in its beam profile, the nominally isotropic mode of an ultrasound transducer, such as a ring transducer, tends to be anisotropic to a certain extent. For example, in the illustrated embodiment, the ultrasound pulses transmitted and received by the ring transducers exhibit an isotropic ratio (ratio of largest to smallest amplitude of beam profile) of approximately 3. Typically, however, this isotropic ratio is sufficient for tracking purposes. Thus, for the purposes of this specification, the signal transmitted or received by an ultrasound transducer is generally isotropic if the measurements for which the ultrasound transducer is used is not substantially affected by the orientation of the ultrasound transducer.

When performing the proximity function, the circumferential mode is also used, so that the transducer will receive the reflected ultrasound signal from the closest endocardial surface, which will allow the endocardial surface to be more easily modeled, as will be discussed in further detail below. It should be noted, however, that the thickness mode of the transducer can be additionally used, so that the transducer will receive the reflected ultrasound signal from the closest endocardial surface in a selected plane, and in particular, the plane perpendicular to the axis of the transducer. In this manner, the additional information provided by the thickness mode provides a more efficient and accurate means of modeling the endocardial surface.

Figure 6:
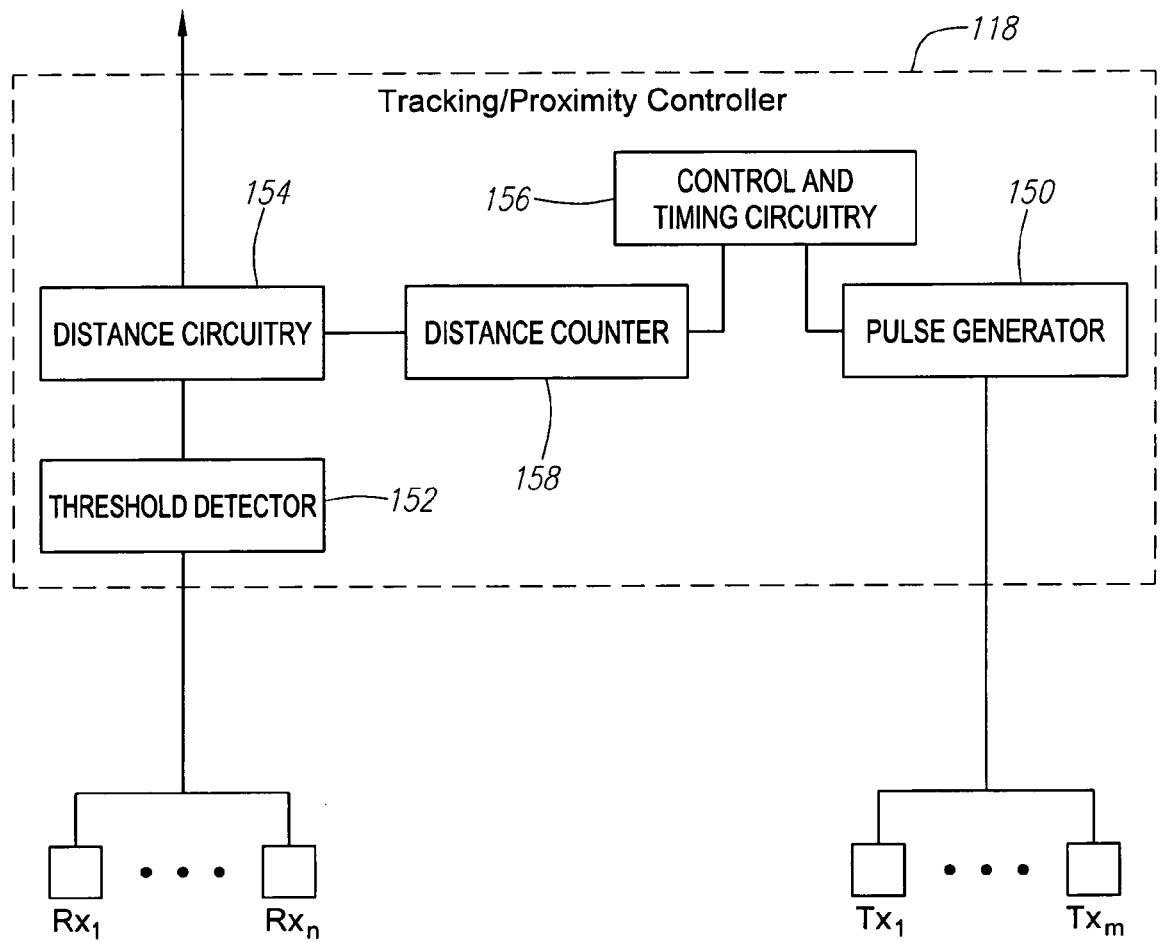
FIG. 6 is a functional block diagram of a tracking/proximity controller used in the medical system of FIG. 1.

Turning now to FIG. 6, the detailed features of the tracking/proximity controller 126 will now be described in the context of several transmitting transducers $TX_1$-$TX_m$ (which may represent the reference elements 116 and the elements 114 when functioning as tracking elements)) and receiving transducers $RX_1$-$RX_n$ (which may represent the elements 114 when used as tracking elements, the reference elements 116, and the elements 114 when used as proximity elements). The controller 126 includes a pulse generator 150 coupled to the transmitting transducers TX, a threshold detector 152 coupled to the receiving transducers RX, distance circuitry 154 coupled to the threshold detector 152, control and timing circuitry 156 coupled to the pulse generator 150, and a distance counter 158 coupled to the control and timing circuitry 156.

The pulse generator 150 is configured for generating electrical pulses that are transmitted to the transmitting transducers TX, which convert the electrical pulses into ultrasound pulses. The control and timing circuitry 156 operates the pulse generator 150, such that the pulses are generated at the desired frequency and spacing. In the illustrated embodiment, the electrical pulses are 1 MHz pulses that are transmitted at a rate of one pulse per millisecond. The control and timing circuitry 156 also controls the multiplexing between the pulse generator 150 and the transmitting transducers TX, such that the elements are stimulated by the electrical pulses in a sequential fashion. Thus, the control and timing circuitry 156 will cause the first transmitting transducer $TX_1$ to transmit an ultrasound pulse (or pulses in the case where the transducer is operated in multiple vibrational modes), then the second transmitting transducer $TX_2$, and so on until the last transmitting transducer $TX_m$ transmits an ultrasound pulse. The control and timing circuitry 156 will then cycle through the transmitting transducers TX again.

Coincident with the transmission of each electrical pulse, the control and timing circuitry 156 is configured for triggering the distance counter 158 to begin counting from zero. The running count value of the distance counter 158 provides a measure of time from the transmission of the ultrasound pulse. This distance counter 158 is reset to zero upon the transmission of the next ultrasound pulse. After each ultrasound pulse has been transmitted, the receiving transducers RX receive and convert the ultrasound pulse into a respective electrical pulse.

The threshold detector 152 is configured for detecting the electrical pulses that are above a threshold level, e.g., a voltage level. In the case where the transmitted ultrasound pulse is generally isotropic (e.g., when a cylindrical ring transducer is operated in a circumferential mode), the threshold detector 152 should be capable of detecting an electrical pulse induced by an ultrasound pulse received from any direction in three-dimensional space. In the case where the transmitted ultrasound pulse is anisotropic, but is generally transmitted within a plane (e.g., when a cylindrical ring transducer is operated in a thickness mode), the threshold detector 152 should be capable of detecting an electrical pulse induced by an ultrasound pulse received from any direction in that plane.

Upon receipt of each detected electrical pulse from the threshold detector 152, the distance circuitry 154 reads the current count from the distance counter 158, which provides a distance measurement between the corresponding receiving transducer RX and the current transmitting transducer TX in the form of an elapsed time between the transmission of the transmit pulse and the detection of the receive pulse. The distance circuitry 154 listens for the transmitted pulse within a time window, e.g., 100 μsec. The time window may begin immediately or shortly after the transmitted pulse has been transmitted. In determining the time of detection of the transmitted pulse by each receiving transducer, the distance circuitry 154 interprets the first signal that the threshold detector 152 detects within the time window as the received pulse. In the case where operation of the transmitting transducer TX in two vibrational modes is desired, the distance circuitry 154 will interpret the first and second signals that the threshold detector 152 detects within the time window as received pulses, and will accordingly read the current count from the distance counter 158 twice.

It should be noted that, for purposes of simplicity, a single threshold detector 152 and distance circuitry 154, is illustrated. In order to correlate each received electrical pulse with the corresponding transducer RX that received it, a separate threshold detector 152 and distance circuitry 154 will preferably be associated with each receiving transducer RX. In the case where two vibration modes are desired to be detected, the corresponding threshold detector 152 will comprise two band-pass filters (not shown), the first of which is centered at the resonant frequency of the circumferential mode, and the second of which is centered at the resonant frequency of the thickness mode.

It should also be noted that there is typically a latency associated with the transmission and reception of an ultrasound signal. This latency is about equal to the wavelength of the ultrasound signal, and as such, is preferably subtracted from the net time of flight to more accurately reflect the distance between the respective transducers. For example, in the RPM system, 2.6 mm, which is close to the 3 mm wavelength of the ultrasound signal, is subtracted from the measured distance.

As illustrated in FIG. 7, the distance information acquired by the controller 126 can be arranged in an eleven-by-fourteen matrix of time values $t_1$-$t_{83}$ defined by eleven transmitting transducers on one side (eight reference elements 116 and three elements 114 when used as proximity elements) (TXVR1-11) and fourteen receiving transducers on the other side (eight reference elements 116 and three elements 114 when used as proximity elements (TXVR1-11), and three elements 114 when used as tracking elements (RX1-3). Note that the only transceivers that transmit to themselves are the proximity elements TXVR9-11, and thus, the identity matrix entries of the transceivers TXVR1-9 are blank. In the case where the elements 114 (TXVR9-11) are operated in two modes, each of the corresponding entries in the matrix will have two time values, as illustrated in FIG. 8.

Figure 9:
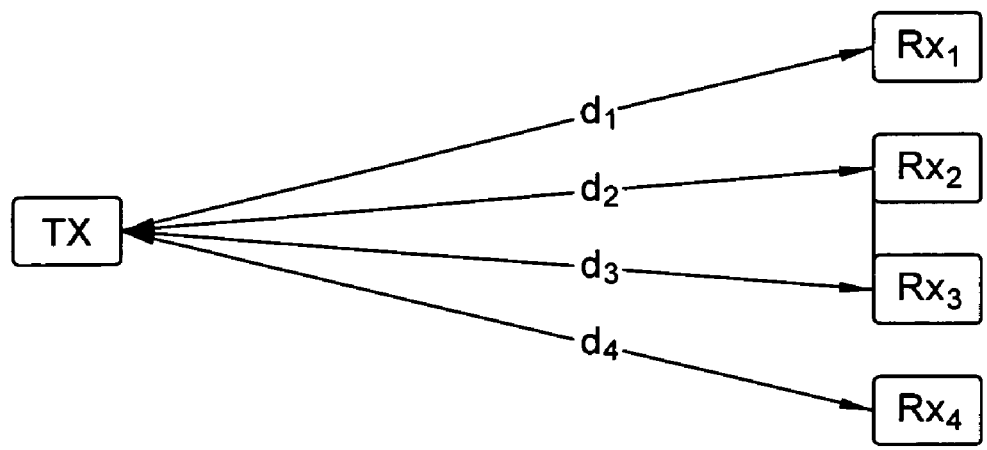
FIG. 9 is a functional block diagram of a positional arrangement between a plurality of ultrasound receiving transducers and an ultrasound transmitting transducer.

As previously stated, the tracking/proximity processor 120 is configured for determining the positional coordinates of the tracking/proximity elements 114 within the coordinate system. The processor 120 accomplishes this by first determining the actual distances between the tracking/proximity elements 114 and reference elements 116 based on the time values obtained from the distance matrix illustrated in FIG. 7. For example, referring to FIG. 9, a transmitting transducer TX and four receiving transducers RX1-4 are shown separated from each other by respective distances $d_1$-$d_4$. To measure the distances $d_1$-$d_4$ between the transmitting transducer TX and the receiving transducers RX1-4, the equation d=vt can be used, where d is the distance between the transmitter and receiver, v is the velocity of the ultrasound signal within the medium (i.e., blood), and t is the time that it takes for the ultrasound signal to travel between the transmitting transducer TX and respective receiving transducer RX. To simplify the distance computations, the velocity of the ultrasound signal may be assumed to be constant. This assumption typically only produces a small error, since the velocity of ultrasound propagation is approximately the same in body tissue and blood.

After the actual distances between the tracking/proximity elements 114 and reference elements 116 have been determined, the processor 120 establishes a three-dimensional coordinate system in which all spatial measurements will be taken by triangulating the distances between the reference elements 116, and determines the positional coordinates (x, y, z) of each of the tracking elements 114 within that coordinate system by triangulating the distances between the reference elements 116 and the tracking elements 114. In the illustrated embodiment, the reference catheters 140 may be affixed within selected regions of the heart 10 in order to establish an internal three-dimensional coordinate system. In this manner, general movement of the patient's body need not be compensated for.

For example, the first two dimensions of the coordinate system can be provided by placing a reference catheter 140 within the coronary sinus (CS) (not shown) of the heart, thereby disposing its reference elements 116 in a two-dimensional plane. The third dimension can be provided by placing another reference catheter 140 within the right ventricular (RV) apex (not shown) of the heart to dispose its reference elements 116 off of the two-dimensional plane. Notably, only four reference elements 116 are needed to provide the three dimensions. Any remaining reference elements 116 can be used to improve the accuracy of the triangulation process. Alternatively, the reference elements 116 may be located outside of the patient's body, e.g., affixed to the patient's skin, in order to establish an external three-dimensional coordinate system.

Additional details on determining the positions of ultrasound transducers within a three-dimensional coordinate system can be found in U.S. Pat. No. 6,490,474 and U.S. patent application Ser. No. 09/128,304, entitled "A dynamically alterable three-dimensional graphical model of a body region," which are fully and expressly incorporated herein by reference.

As will be described in further detail below, the positional coordinates of the tracking/proximity elements 114 can ultimately be used to graphically reconstruct the distal end of the mapping/ablation catheter 108 (as well as any reference catheters 140), track the movement of the mapping/ablation catheter 108 within the heart, and in conjunction with the mapping data obtained from the mapping processor 110, generate an electrophysiological map.

Figure 10:
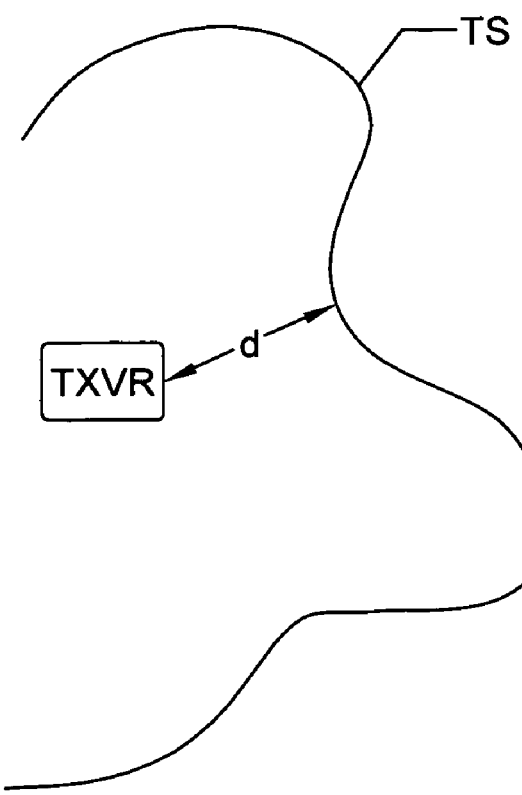
FIG. 10 is a functional block diagram of a positional arrangement between an ultrasound transceiving transducer and a tissue surface.

As previously stated, the processor 120 is further configured for determining the proximity of the endocardial surface of the heart to each tracking/proximity element 114. The processor 120 accomplishes this by determining the actual distance between each tracking/proximity element 114 and the endocardial surface based on the time values obtained from the distance matrix illustrated in FIG. 7, or alternatively, FIG. 8 if dual mode measurements are desired. For example, referring to FIG. 10, a transducer TXVR is shown surrounded by a tissue surface TS. As can be seen, the distance between the transducer TXVR and the tissue surface TS depends upon the selection of an arbitrary point on the tissue surface TS where the measurement is to be taken. However, the only distance that is relevant is the shortest distance between the transducer TXVR and the tissue surface TS, shown as distance d. In the case where the generally isotropic circumferential mode of a cylindrical ring transducer is used, the shortest distance within three-dimensional space will be relevant. In the case where the anisotropic thickness mode of a cylindrical ring transducer is used, the shortest distance within a single plane will be relevant. In either case, the distance d can be measured using the equation $d=vt/2$, where v is the velocity of the ultrasound signal within the medium (i.e., blood), and t is the shortest time that it takes for the ultrasound signal to travel from the transducer TXVR, to the tissue surface TS, and back to the transducer TXVR as a reflected ultrasound signal.

As will be described in further detail below, the determined distances between the tracking/proximity elements 114 and the endocardial surface of the heart can be coupled with the determined positional coordinates of the tracking/proximity elements 114 to ultimately determine the proximity of the endocardial surface to known positions within the coordinate system, which information can then be used to graphically reconstruct the endocardial surface.

III. Graphical User Interface

Figure 11:
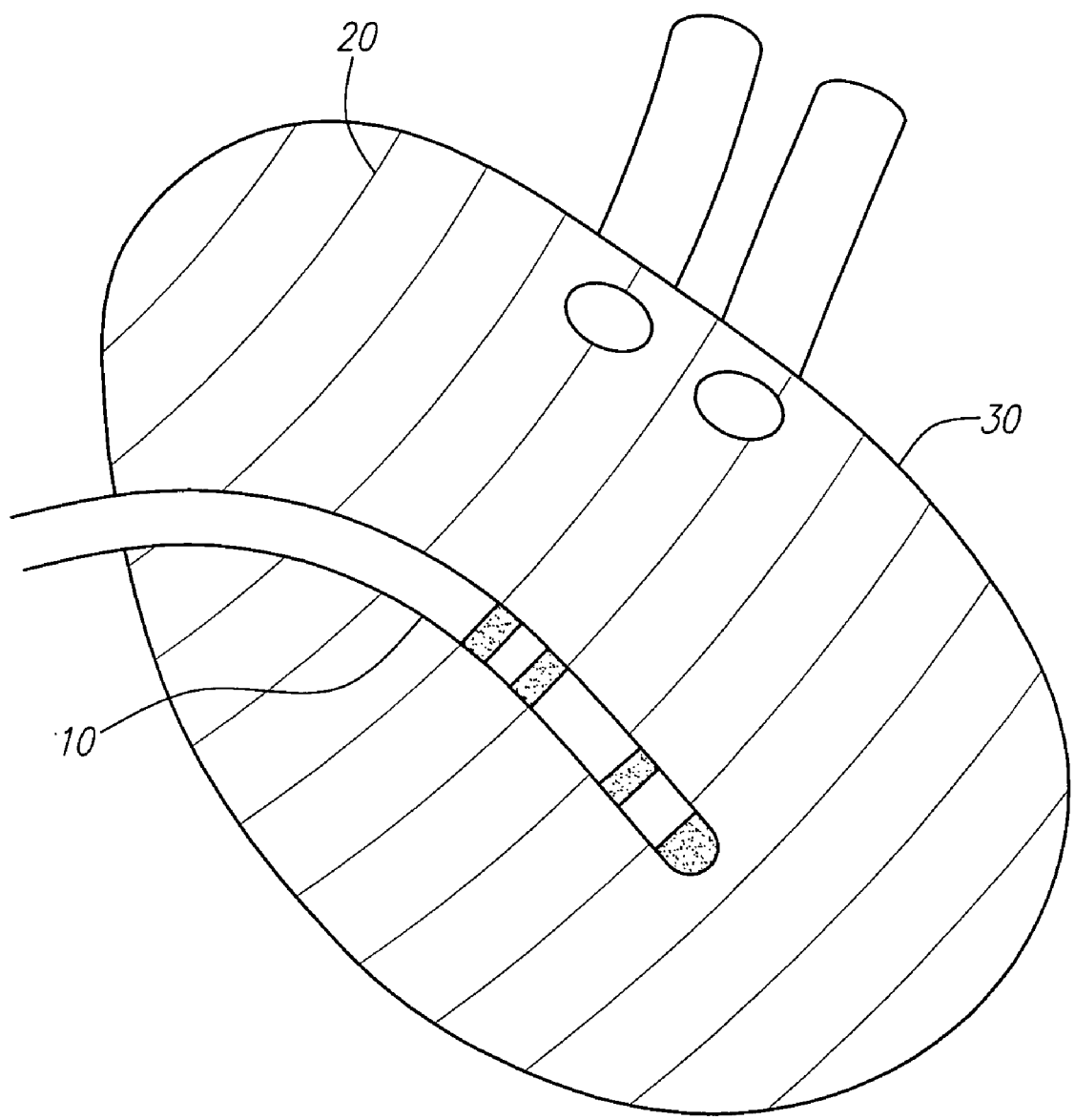
FIG. 11 is a view illustrating graphical representations of a mapping/ablation catheter, an endocardial surface of a heart, an electrical activity map generated by the system of FIG. 1.

Referring still to FIG. 1, the graphical user interface 106 comprises a graphical processor 122, a user input device 124 (such as a mouse 128 and/or keyboard 130), and an output device 126 (such as a monitor), which are configured for displaying and allowing a user to interact with a graphical representation 10 of the mapping/ablation catheter 108, an electrical activity map 20, and a graphical representation 30 of the surface of an internal anatomical structure (in this case, the endocardial surface of a heart), as illustrated in FIG. 11. Optionally, the graphical user interface 106 may graphically generate orifice and vessel representations, the details of which are described in U.S. patent application Ser. No. 10/850,357, entitled "System and Method of Graphically Representing Anatomical Orifices and Vessels," which is expressly incorporated herein by reference.

The graphical processor 122 generates the graphical representation 10 of the catheter 108 by first acquiring from the tracking/proximity subsystem 104 the positions of the tracking/proximity elements 114 within the coordinate system. Once the positional information is acquired, the graphical processor 122 can generate the graphical catheter representation 10 from a pre-stored graphical model of the catheter 108, which can be deformed in accordance with the calculated positional coordinates of the tracking/proximity elements 114 carried by the catheter 108. In the illustrated embodiment, the graphical catheter representation 10 is dynamically generated in real-time. That is, the catheter representation 10 is graphically generated in successive time periods (e.g., once every heartbeat), so that it moves and bends as the actual catheter 108 is moved and bent within the heart chamber. The graphical processor 122 may optionally be configured to generate graphical representations of the reference catheters 140 (not shown) in real-time.

The graphical processor 122 generates the electrical activity map 20 based on the electrical activity information acquired from the mapping/ablation subsystem 102 and the positions of the mapping electrodes 134 geometrically derived from the positions of the tracking elements 114 obtained from the tracking/proximity subsystem 104. This electrical activity map illustrates sites of interest, e.g., electrophysiology recording and ablation sites, for providing subsequent ablative treatment, and can be provided in the form of an isochronal or isopotential map.

Additional details on graphically generating catheters and electrical activity maps within a three-dimensional environment can be found in U.S. Pat. No. 6,490,474 and U.S. patent application Ser. No. 09/128,304, entitled "A dynamically alterable three-dimensional graphical model of a body region," which have previously been incorporated herein by reference.

In the illustrated embodiment, the graphical processor 122 is configured for generating the graphical surface representation 30 using both a passive deformation technique, which involves deforming a graphical anatomical shell to interior geometric shapes as the catheter 108 is moved within the heart, and a snap deformation technique, which involves deforming the graphical anatomical shell to known points on the endocardial surface of the heart.

In performing passive deformation, the graphical processor 122 acquires from the tracking/proximity subsystem 104 the positions of the tracking/proximity elements 114 within the coordinate system and the proximity between the tracking/proximity elements 114 and the endocardial surface 20 (which information can be periodically acquired, e.g., once every heartbeat) as the mapping/ablation catheter 108 is moved around within the left atrium 12, and deforms the surface representation 30 (in particular, an anatomical shell) in accordance with the acquired positional and proximity information.

Figure 12:
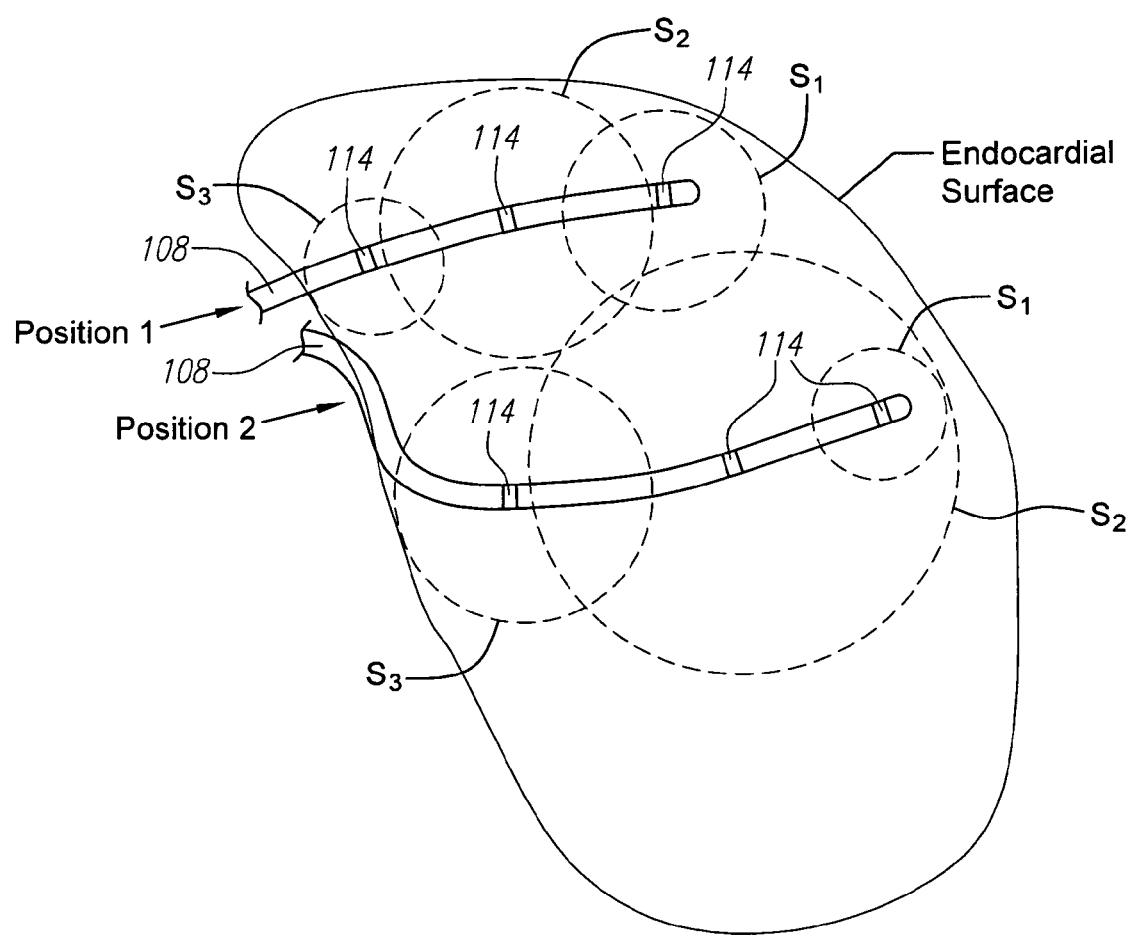
FIG. 12 is a view illustrating the definition of spheres originating from tracking/proximity elements within the heart at two catheter positions.

In particular, the graphical processor 122 models the blood volume within the heart (or heart chamber) with a multitude of geometric shapes that are known to be included within the blood volume. For the purposes of this specification, a geometric shape is any two- or three-dimensional shape. The graphical processor 122 accomplishes this by defining a geometric shape based on each positional coordinate and proximity acquired from the tracking/proximity subsystem 104. In this case, for each heartbeat, three geometric shapes will be defined for the three respective tracking/proximity elements 114. In the illustrated embodiment, each geometric shape takes the form of a sphere having an origin coincident with the acquired positional coordinate of the respective tracking/proximity element 114, and a radius equal to the acquired proximity distance between the respective tracking/proximity element 114 and the endocardial surface. For example, FIG. 12 illustrates the generation of spheres $s_1$, $s_2$, and $s_3$ derived from the positions of the tracking/proximity elements 114 and their proximity to the endocardial surface when the catheter 108 is placed in a first position, and the generation of additional spheres $s_1$, $s_2$, and $s_3$ derived from the positions of the tracking/proximity elements 114 and their proximity to the endocardial surface when the catheter 108 is placed in a second position. Thus, as illustrated in FIG. 13, groups of spheres, the union of which represents the blood volume within the heart or heart chamber, are defined over a period of time as the mapping/ablation catheter 108 is moved around within the heart.

Notably, a sphere is selected as the geometric shape because the ultrasound signal transmitted by each tracking/proximity element 114 is generally isotropic when operated in the circumferential mode (i.e., the geometric shape should match the signal footprint of the tracking/proximity element 114). Thus, it can be assumed that the shortest measured "round trip time-of-flight" of the ultrasound signal does indeed accurately represent a function of, and in particular twice the shortest distance between the endocardial surface and the respective tracking/proximity element 114 in three-dimensional space, and thus, the defined sphere will not fall outside of the blood volume.

Figure 13:
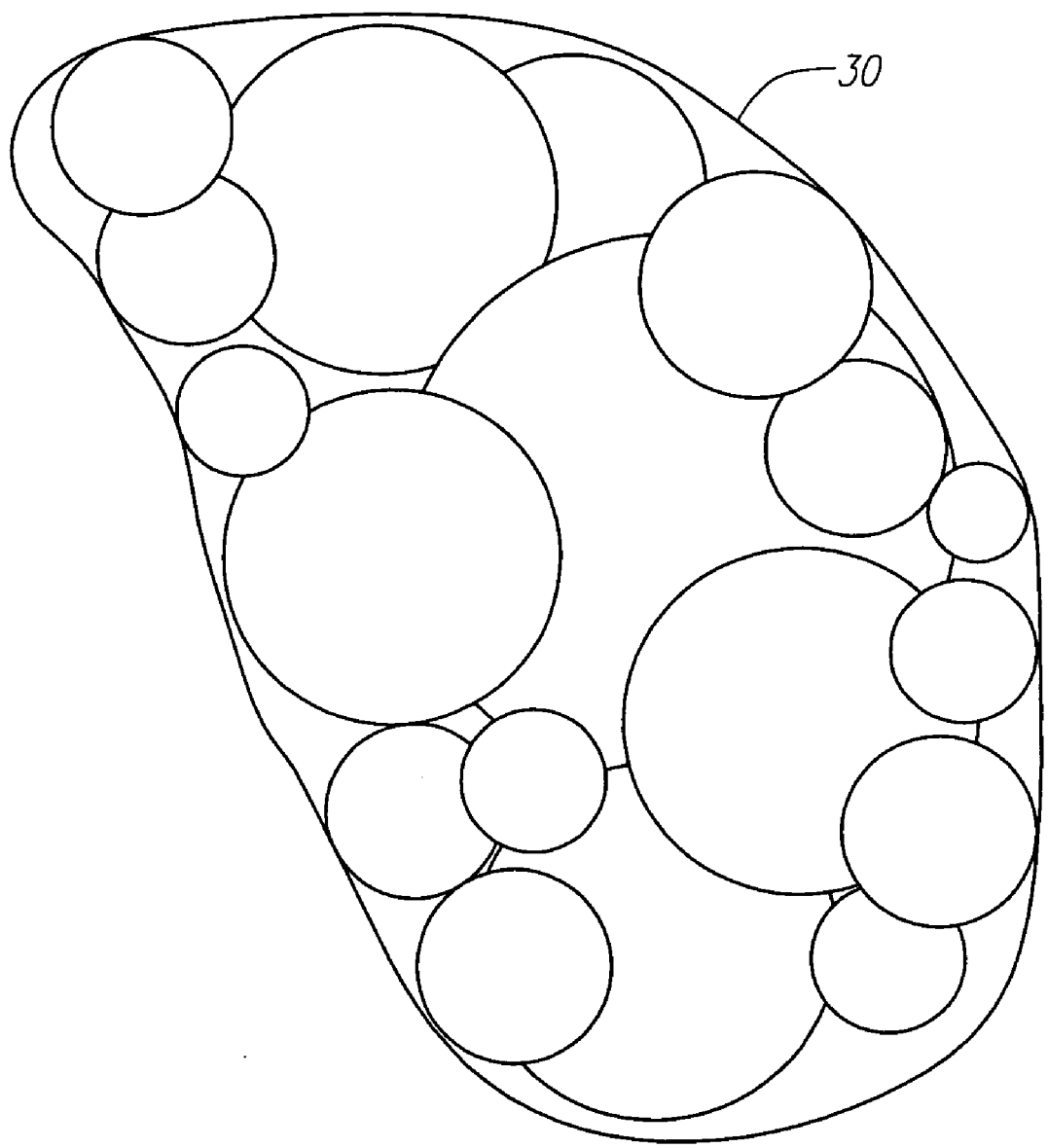
FIG. 13 is a view illustrating the generation of a graphical endocardial surface representation around a union of the spheres defined in FIG. 12.

As the spheres are defined, the graphical processor 122 is configured for creating a graphical anatomical shell around the union of the spheres, as illustrated in FIG. 13. This shell can be created using the algorithm described in "An Implicit Surface Polygonizer", Jules Bloomenthal, Graphics Gems IV, Academic Press Professional, 1994, which is expressly incorporated herein by reference. This algorithm creates a polygon shell that can be rendered graphically given an input surface defined by implicit functions. An implicit function has the form $f(x,y,z)=0$. For a sphere with radius r centered at x', y', z', this function has the form $(x-x')^2+(y-y')^2+(z-z')^2-r^2=0$. The outer surface of the union of multiple spheres $f_1(x,y,z)$ i=1 ... N is represented by the function $$\min_i \{f_i(x, y, z)\} = 0.$$

Because the union of the spheres represents the blood volume, the resulting anatomical shell accurately represents the endocardial surface of the heart, which contains the blood volume. Significantly, when representing the blood volume, the use of three-dimensional shapes, such as spheres, provides much more information than does the use of points, thereby allowing the endocardial surface to be graphically reconstructed more efficiently and accurately.

Figure 14:
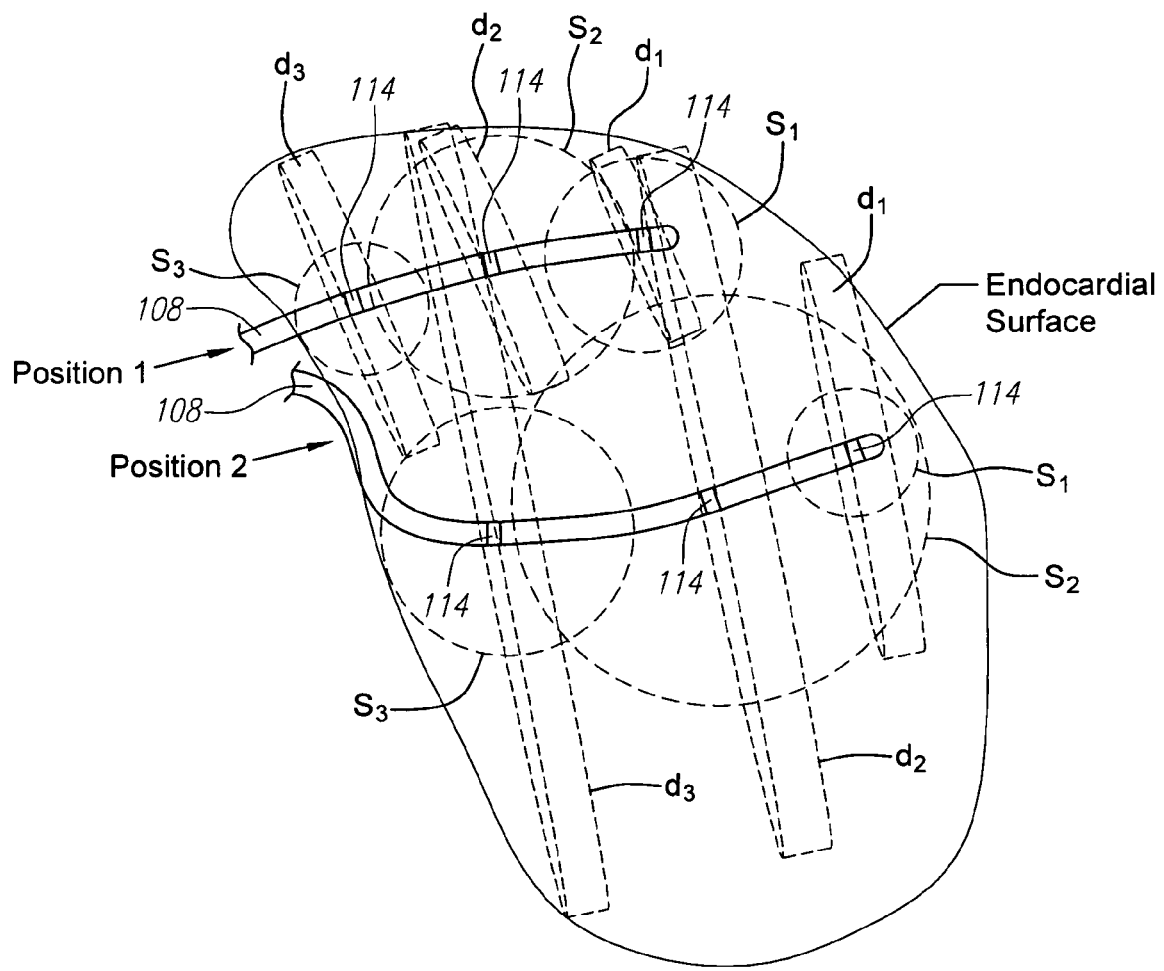
FIG. 14 is a view illustrating the definition of spheres and disks originating from tracking/proximity elements within the heart at two catheter positions.
Figure 15:
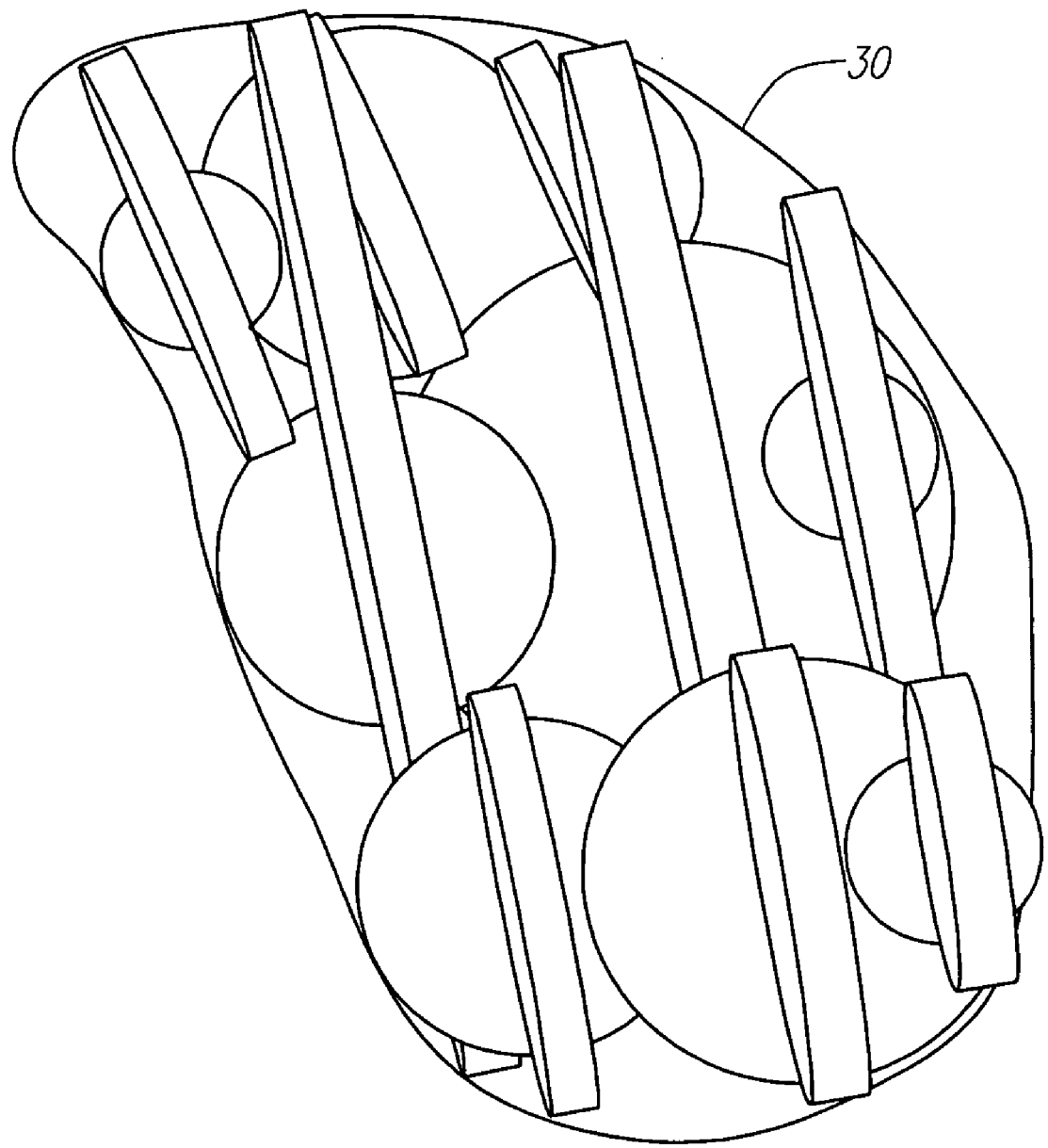
FIG. 15 is a view illustrating the generation of a graphical endocardial surface representation around a union of the disks and spheres defined in FIG. 12.

Geometric shapes other than spheres can be defined by the graphical processor 122, as long as such geometric shapes match the signal footprint generated by the tracking/proximity elements 114. For example, if the thickness mode of the tracking/proximity elements 114, which produces ultrasound signals that radially extend outward in a single plane, is utilized, disks (or two-dimensional circles) in addition to spheres can be defined, as illustrated in FIG. 14. The same implicit function technique described above can be used by approximating the two-dimensional circle as a flattened three dimensional ellipse, i.e., $$\left(\frac{x}{r}\right)^2 + \left(\frac{y}{r}\right)^2 + \left(\frac{z}{\varepsilon}\right)^2 = 0,$$

where r is the radius of the circle and $\varepsilon$ is a small number say 1 mm representing the height of the flattened ellipse. Ellipses with arbitrary orientation and position can be created by applying a rotation and shift of the x, y, z parameters in the above equation. The graphical processor 122 can then deform the anatomical shell around the union of the spheres and circles, as illustrated in FIG. 15. As such, twice as many geometric shapes, and thus, twice as much information, is provided, thereby making the deformation process more efficient and accurate.

In performing snap deformation, the graphical processor 122 first acquires the positions of the tracking/proximity elements 114 within the coordinate system from the tracking/proximity subsystem 104 when the distal catheter tip is touching the endocardial surface. The graphical processor 122 then geometrically derives the position of the catheter tip within the coordinate system from the acquired positions of the tracking/proximity elements 114, and deforms the anatomical shell to be coincident with the position of the catheter tip.

Figure 16:
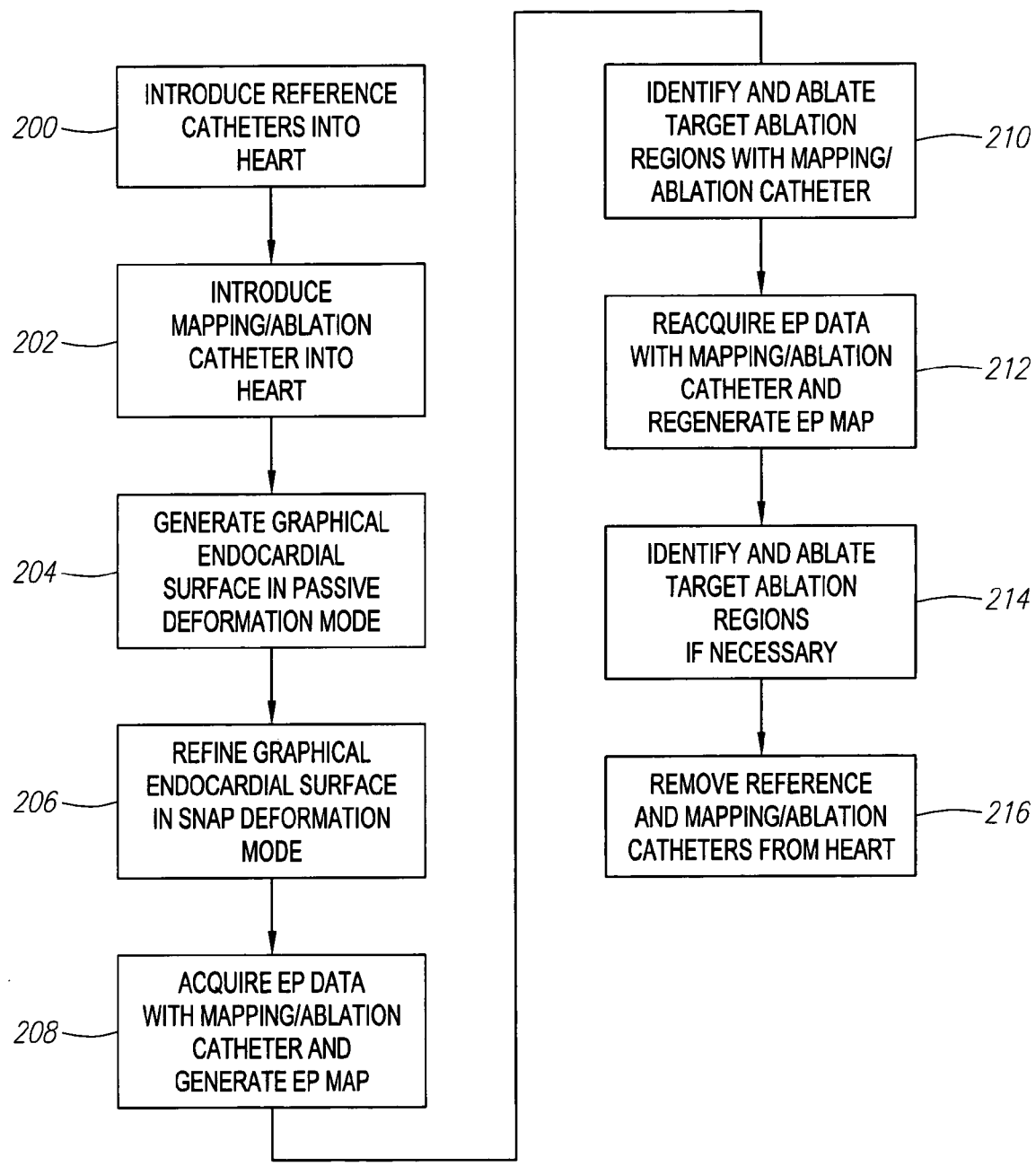
FIG. 16 is a flow diagram illustrating a detailed method of tracking a mapping/ablation catheter within a heart, and treating an aberrant conductive path using the medical system of FIG. 1.

Having described the structure of the medical system 100, one method of using the system 100 to locate and treat an aberrant conductive pathway within the heart 10, such as those typically associated with atrial fibrillation, will now be described with reference to FIG. 16. First, under fluoroscopy, the reference catheters 140 are intravenously introduced into the heart, and in particular, within the coronary sinus (CS) and right ventricle (RV) apex, so that the reference elements 116 are fixed within a three-dimensional arrangement (step 200). During introduction of the reference catheters 140, the tracking/proximity subsystem 104 may be operated to transmit signals between the reference elements 116, so that the locations of the distal ends of the reference catheters 140 can be determined and graphically displayed on the monitor 126. Next, the mapping/ablation catheter 108 is introduced into the heart under fluoroscopy (step 202). During the introduction of the catheter 108, the tracking/proximity subsystem 104 may be operated to transmit signals between the reference elements 116 and the tracking elements 114, so that the distal end of the catheter 108 can be determined and graphically displayed on the monitor 126.

The graphical processor 122 is then operated in the "Passive Deformation" mode, and the catheter 108 is moved around within the selected chamber of the heart as the position of the distal catheter tip is determined (step 204). As a result, the graphical processor 122 generates the endocardial surface representation 30, which begins as a generally spherical shape, and deforms it to coincide with the union of the geometric shapes (in particular, spheres and/or disks or circles) defined in accordance with the positions of the tracking/proximity elements 114 and their proximity to the endocardial surface. The graphical processor 122 can then be operated in the "Snap Deformation" mode to refine the endocardial surface representation 30, in which case, the distal tip of the catheter 108 will be placed against selected regions of the endocardial surface, so that the graphical processor 122 can deform the surface representation 30 to the surface points acquired by the distal catheter tip 120 (step 206). During its deformation in both Passive Deformation and Snap Deformation modes, the endocardial surface representation 30 is displayed on the monitor 126. The graphical processor 122 can optionally be operated to graphically generate orifices and vessels within and outside of the heart, the details of which are described in U.S. patent application Ser. No. 10/850,357, entitled "System and Method of Graphically Representing Anatomical Orifices and Vessels," previously incorporated by reference.

The mapping processor 110 is then operated to record electrical activity within the heart with the mapping/ablation catheter 108 and derive mapping data therefrom. The graphical processor 122 acquires this mapping data and generates the electrical activity map 20, which is then displayed on the monitor 126 over the endocardial surface representation 30 (step 208). If an aberrant region is identified, the user places the distal tip of the catheter 108 into contact with the targeted ablation region, and the RF generator 112 is operated to therapeutically create a lesion on the endocardial surface (step 210). After the lesion has been completed, the mapping processor 110 can again be operated to ensure that the heart disease has been successfully treated by reacquiring the mapping data and regenerating the electrical activity map 20 for display on the monitor 126 over the endocardial surface representation 30 (step 212). If additional aberrant conductive pathways have been found, the target ablation regions are again identified and ablated (step 214). If no aberrant conductive pathways have been found, the reference catheters 140 and mapping/ablation catheter 108 can then be removed from the heart (step 216).

Figure 17:
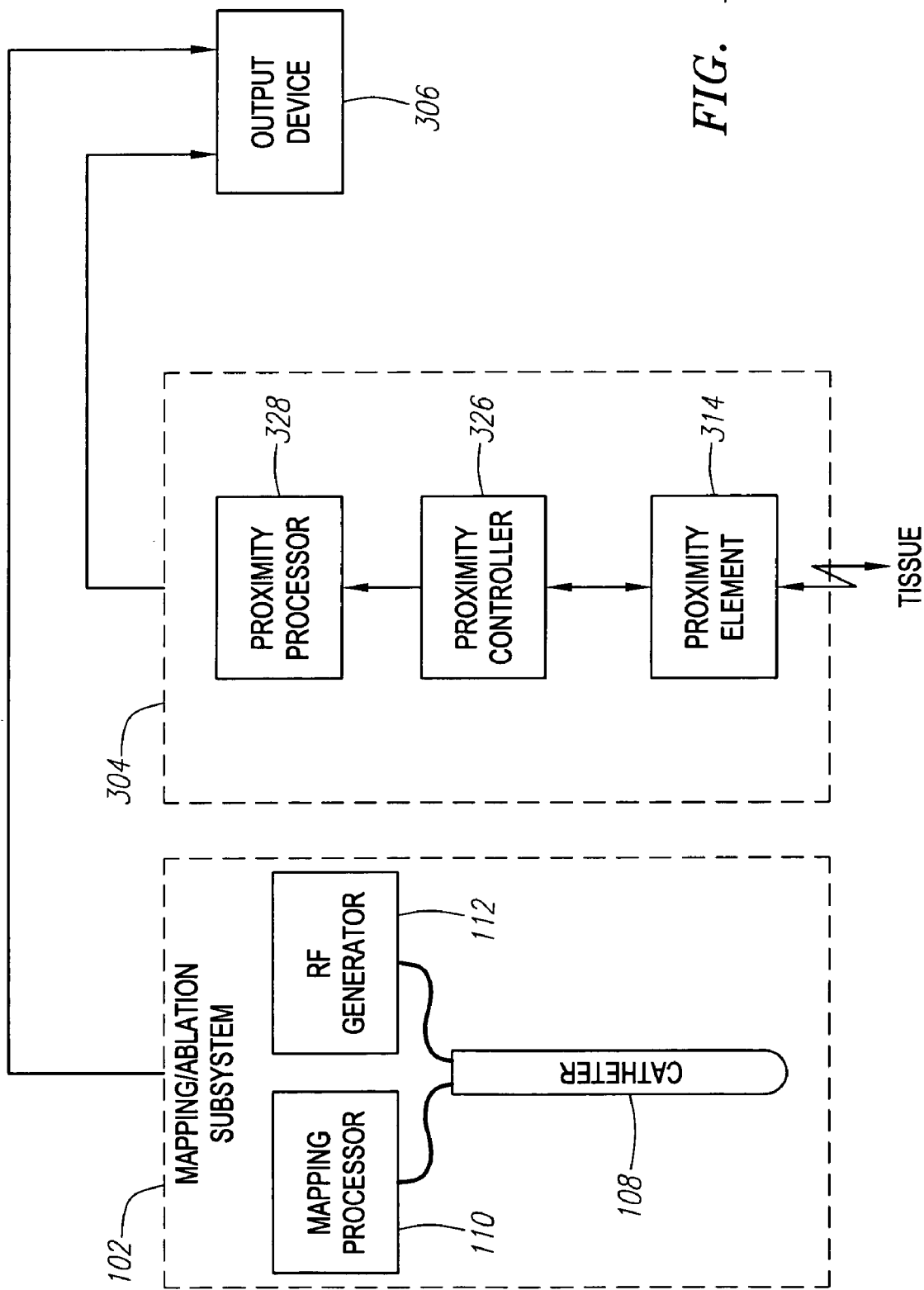
FIG. 17 is a functional block diagram of another preferred embodiment of a medical system constructed in accordance with the present inventions.

Referring to FIG. 17, another exemplary medical system 300 constructed in accordance with the present invention will be described. Like the previously described medical system 100, the medical system 300 is particularly suited for mapping and treating a heart with catheters. The medical system 300 lends itself well to applications where it is desirable to determine the contact between a tissue and a catheter, such as a therapeutic catheter, without having to implement a catheter tracking system. However, the medical system 300 can be combined with a catheter tracking system, such as the prior art RPM and CARTO EP systems, to facilitate graphical reconstruction of the endocardial surface of the heart.

To this end, the medical system 300 generally comprises (1) the previously described mapping/ablation subsystem 102 for mapping and ablating tissue within the heart; (2) a proximity subsystem 304 for generating and receiving ranging signals used to measure proximity between objects within the heart; and (3) an output device, such as a monitor and/or speaker, for conveying mapping and proximity information to the user. It should be noted that the elements illustrated in FIG. 17 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

Referring still to FIG. 17, the proximity subsystem 304 includes a single proximity element 314; (2) a proximity controller 326 for coordinating the transmission signals from the proximity element 314 and the reception of reflected signals by the proximity element 314; and (3) a proximity processor 328 for determining the proximity between the proximity element 314 and at least two locations on the endocardial surface of the heart and determining contact between a portion of the mapping/ablation catheter 108, and in particular, contact between the distal-most electrode 134 and the endocardial surface.

Figure 18:
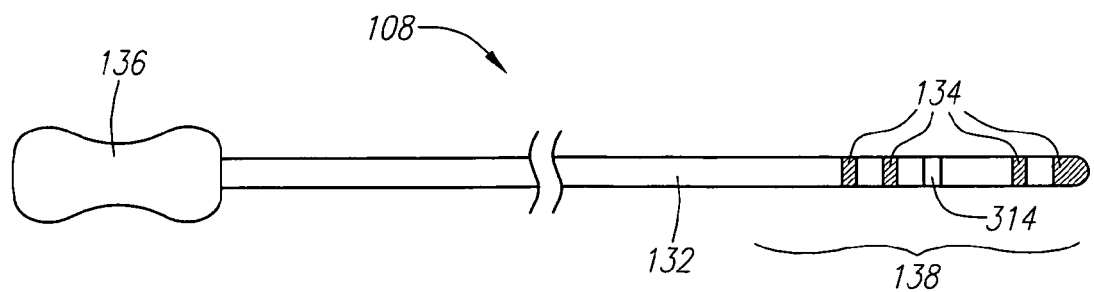
FIG. 18 is a plan view of a mapping/ablation catheter used in the medical system of FIG. 16.

As shown in FIG. 18, the proximity element 314 is physically carried by the distal end of the mapping/ablation catheter 108. In the illustrated embodiment, the proximity element 314 is located on the rigid or semi-rigid straight section 138 proximal to the distal-most electrode 134. In this manner, the proximity of the distal-most electrode 134, or any catheter portion along the straight section 138, can be more easily determined based on proximity measurements taken at the proximity element 314. In the illustrated embodiment, the proximity subsystem 304 is ultrasound-based, and thus, the proximity element 314 takes the form of an ultrasound transducer, which is well-suited for serving as transceiver for determining proximity to tissue.

Figure 19:
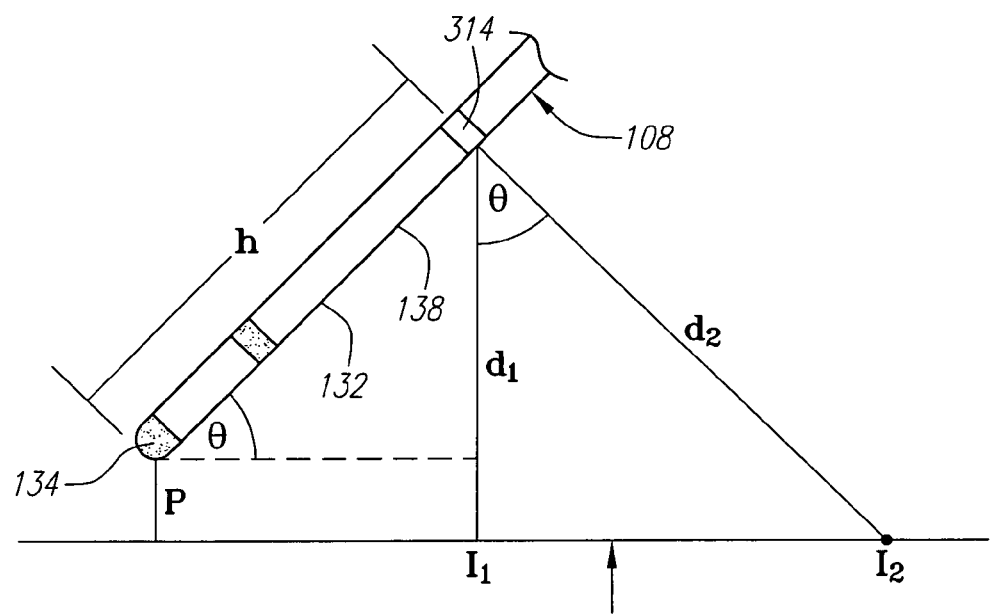
FIG. 19 is plan view illustrating the positional arrangement between the mapping/ablation catheter of FIG. 18 and an endocardial surface.

Referring to FIG. 19, the controller 326 operates the proximity element 314 as a transceiver to transmit signals from the proximity element 314 to two locations $l_1$ and $l_2$ on the endocardial surface, and for receiving the reflected signals from the endocardial surface, so that two different proximities or distances $d_1$, $d_2$ between the proximity element 314 and the endocardial surface can be determined by the processor 328, as will be described in further detail below. To allow determination of the distances $d_1$, $d_2$ between the proximity element 314 and the two endocardial surface locations $l_1$, $l_2$, the proximity element 314 is operated in two vibration modes, and in particular, the circumferential and thickness modes. As previously discussed, both modes can be simultaneously generated by stimulating the proximity element 314 with an electrical pulse having a relatively short width that spreads the harmonic frequencies over a broad range that includes the resonant frequencies.

Figure 20:
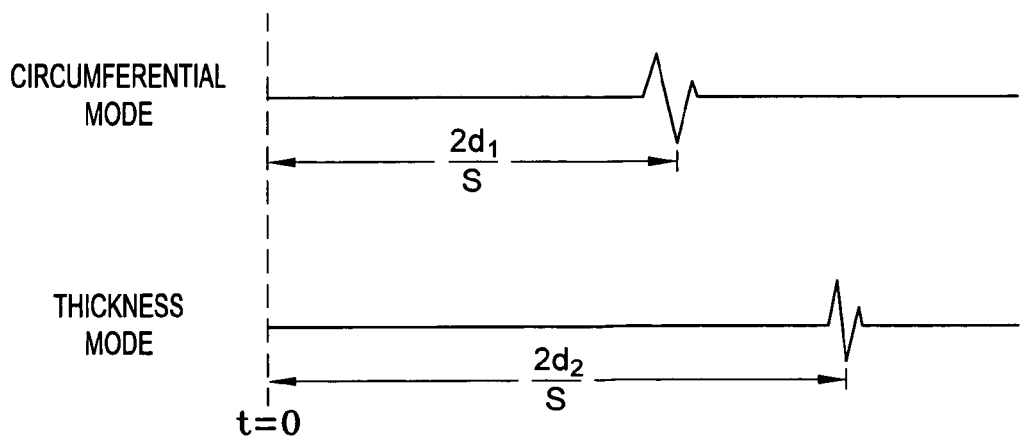
FIG. 20 is a timing diagram illustrating the electrical signals induced by the receipt of dual-mode ultrasound signal transmitted by a proximity element used in the system of FIG. 18.

That is, when an electrical signal is applied to the proximity element 314 by the controller 326, the proximity element 314 vibrates at the resonant frequencies corresponding to the circumferential and thickness vibration modes. As previously discussed above with respect to the tracking/proximity element 114, this causes ultrasound signal to propagate away from the proximity element 314, a portion of which reflects off of the endocardial surface and is directed back to the proximity element 314, which converts the reflected ultrasound signal back into an electrical signal. In this case, two electrical pulses (shown in FIG. 20) corresponding to the circumferential and thickness vibration modes, are induced upon receipt of the reflected ultrasound signals. It should be appreciated that the use of circumferential and thickness modes is particularly useful for determining the distances $d_1$, $d_2$.

In particular, the distance $d_1$ represents the shortest distance between the proximity element 314 and the endocardial surface in three-dimensional space, and the distance $d_2$ represents the shortest distance between the proximity element 314 and the endocardial surface in a plane that extends through the proximity element 314 and is perpendicular to the axis of the straight section 138 of the catheter shaft 132. Thus, when the proximity element 314 is operated in a circumferential mode, the transmitted ultrasound signal is generally isotropic, and thus, the first instance of an ultrasound signal received by the proximity element 314 at the resonant frequency of the circumferential mode (illustrated in FIG. 20), will have traveled along a path corresponding to the distance $d_1$. Thus, the controller 326 can calculate the fastest "round trip time-of-flight" of the ultrasound signal between the proximity element 314 and endocardial surface location $l_1$ based on the elapsed time between the transmission of the electrical signal that induces transmission of the ultrasound signal and the receipt of the electrical signal (at the resonant frequency of the circumferential mode) induced by the receipt of the reflected ultrasound signal.

When the proximity element 314 is operated in a thickness mode, the transmitted ultrasound signal is anisotropic, but generally focused in a plane perpendicular to the axis of the straight shaft section 138, and thus, the first instance of an ultrasound pulse received by the proximity element 314 at the resonant frequency of the thickness mode (illustrated in FIG. 20), will have traveled along a straight line corresponding to the distance $d_2$. Thus, the controller 326 can calculate the fastest "round trip time-of-flight" of the ultrasound signal between the proximity element 314 and endocardial surface location $l_2$ based on the elapsed time between the transmission of the electrical signal that induces transmission of the ultrasound signal and the receipt of the electrical signal (at the resonant frequency of the circumferential mode) induced by the receipt of the reflected ultrasound signal.

The detailed features of the proximity controller 326 can be the same as that of the tracking/proximity controller 126 described above with respect to FIG. 6, with the exception that the tracking functionality of the controller 126 is not needed. That is, along with the pulse generator 150, control and timing circuitry 156, and distance counter 158, the proximity controller 326 need only include the threshold detector 152 (which includes band-pass filters (not shown) to filter the respective resonant frequencies of the circumferential and thickness modes) and the distance circuitry 154 previously associated with one of the tracking/proximity elements 114.

As previously stated, the proximity processor 320 is configured for determining contact between the distal-most electrode 134 and the endocardial surface. The processor 320 accomplishes this by first determining the actual distances $d_1$, $d_2$ between the proximity element 314 and the endocardial surface locations $l_1$, $l_2$ based on the roundtrip time-of-flight values. The distances $d_1$, $d_2$ can be measured using the equations $d_1=vt_1/2$, $d_2=vt_2/2$ where v is the velocity of the ultrasound signal within the medium (i.e., blood), and $t_1$ and $t_2$ are the shortest times that it takes for the ultrasound signal to travel from the proximity element 314 to the respective endocardial surface locations $l_1$ and $l_2$, and back to the proximity element 314 as a reflected ultrasound signal. Having calculated the distances $d_1$, $d_2$, the proximity processor 320 can then calculate the angle θ formed between the straight section 138 of the catheter shaft 132 and the endocardial surface using the equation $\theta = \cos^{-1}(d_1/d_2)$.

The proximity processor 320 can then calculate the proximity between the distal-most electrode 134 and the endocardial surface using the equation $p=d_1-h \sin \theta$, where p is the proximity between a point on the straight shaft section 138, and h is the known distance between the proximity element 314 and the point along the axis of the straight shaft section 138. In the case where proximity between the distal-most ablation electrode 134 and the endocardial surface is desired, the point represents the location of the distal-most ablation electrode 134, and the distance h is the distance between the distal-most ablation electrode 134 and the proximity element 314.

Once the proximity processor 320 has determined the proximity p, it transmits it to the output device 306, which visually conveys the proximity information (either textually or symbolically) to the user and/or auditorily conveys the proximity information to the user. The output device 306 may also display electrical activity information received from the mapping processor 110.

Figure 21:
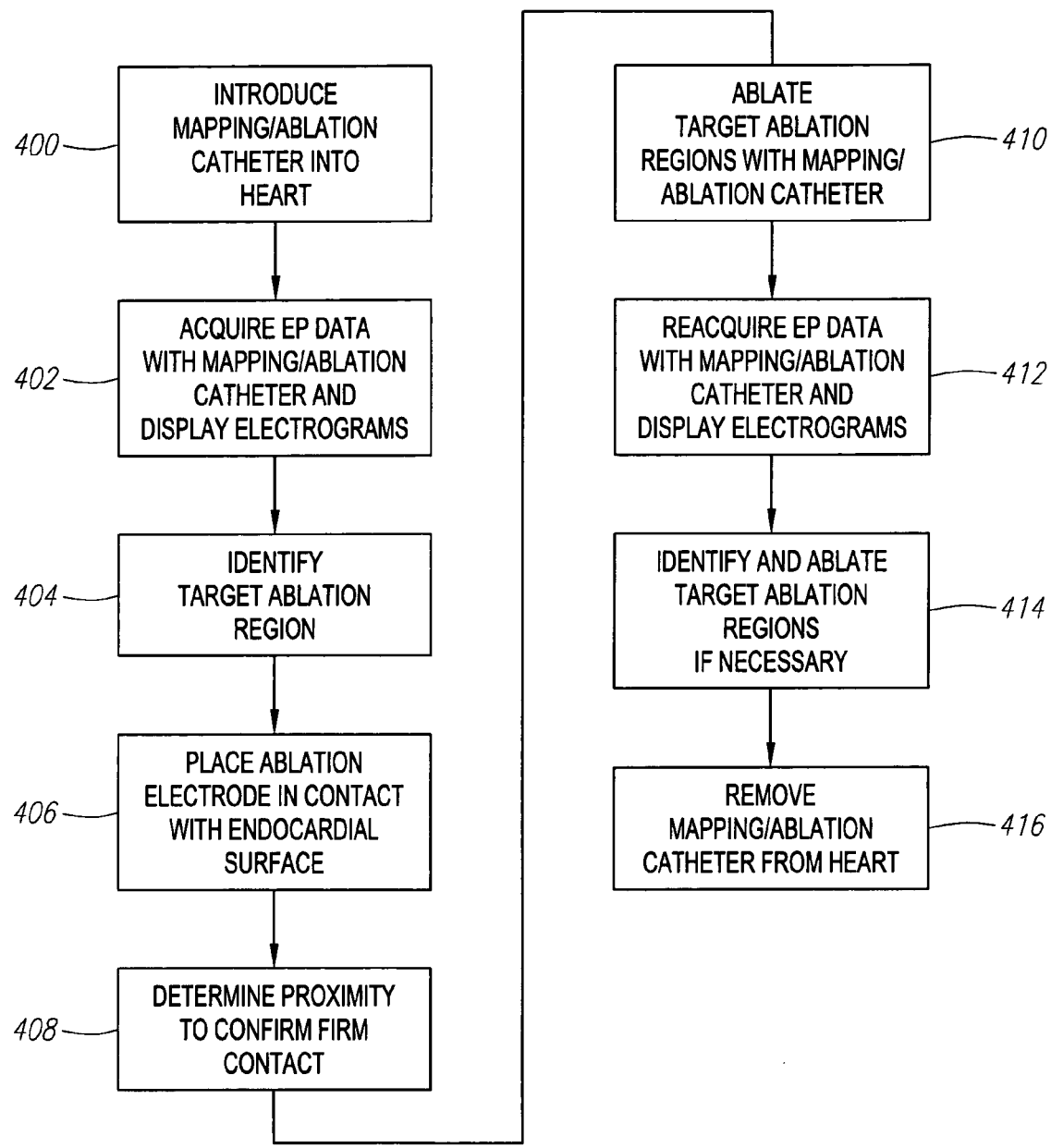
FIG. 21 is a flow diagram illustrating a method of treating an aberrant conductive path using the medical system of FIG. 18.

Having described the structure of the medical system 300, one method of using the system 300 to locate and treat an aberrant conductive pathway within the heart 10, such as those typically associated with atrial fibrillation, will now be described with reference to FIG. 21. First, under fluoroscopy, the mapping/ablation catheter 108 is introduced into the heart under fluoroscopy (step 400). The mapping processor 110 is then operated to record electrical activity within the heart with the mapping/ablation catheter 108 and derive mapping data therefrom, which can be displayed on the output device 306 in electrogram format (step 402). Based on the electrograms, the aberrant region is identified (step 404), and the user then places the distal tip of the catheter 108 into contact with the targeted ablation region (step 406). The proximity subsystem 304 is operated to determine the proximity between the ablation electrode 134 and the endocardial surface, thereby confirming firm contact therebetween (step 408). That is, if the output device 306 indicates that the proximity between the ablation electrode 134 and the endocardial surface is zero, firm contact is established. Once firm contact is confirmed, the RF generator 112 is operated to therapeutically create a lesion on the endocardial surface (step 410). After the lesion has been created, the mapping processor 110 can again be operated to ensure that the heart disease has been successfully treated by reacquiring the mapping data and displaying the electrograms on the output device 306 (step 412). If additional aberrant conductive pathways have been found, the target ablation regions are again identified and ablated (step 414). If no aberrant conductive pathways have been found, the mapping/ablation catheter 108 can then be removed from the heart (step 416).

It should be appreciated that, although there are other means for determining the proximity between the a catheter and endocardial surface, the use of a single dual-mode proximity element provides distinct advantages over these other means. For example, it may be possible to locate a single proximity element on the region of the catheter, such as the distal tip, for which the proximity determination is particularly relevant. However, another operative element, such as an ablation electrode, must typically be located at this relevant catheter region, thereby requiring the proximity element to be collocated with the operative element, which cannot be practically accomplished, or at the least, imposes severe design constraints on the catheter. In contrast, a dual-mode proximity element can be located remotely from the relevant catheter region on which the operative element is to be mounted. As another example, it may be possible to locate multiple proximity elements along the catheter. However, the use of multiple proximity elements adds expense and adds complexity to the proximity controller.

It should be also appreciated that the use of a dual-mode proximity element can be used to determine the proximity of a catheter and a tissue surface for purposes other than ensuring firm contact between an electrode and the tissue during an ablation procedure. For example, the dual-mode proximity element can be operated to determine the proximity between mapping electrodes and tissue, so that electrograms for which the source electrodes were more than a given distance away from tissue can be rejected. As another example, the dual-mode proximity element can be used with prior art three-dimensional medical systems, such as the RPM or CARTO EP systems. In the case of the RPM system, the dual-mode proximity element can be used to confirm contact between the distal tip of the catheter and the tissue during the acquisition of surface points during the snap deformation mode. In the case of the CARTO EP system, which relies entirely on the acquisition of surface points to generate the graphical surface representation, the dual-mode proximity element can likewise be used to confirm contact between the distal tip of the catheter and the tissue.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of graphically creating a representation of an anatomical structure, comprising:
    moving the distal end of an elongated probe within the anatomical structure;
    generating data, based on signals emitted by the probe, while the distal probe end is moved within the anatomical structure;
    defining geometric shapes, based on the generated data, within a coordinate system, each of the geometric shapes originating from the distal probe end; and
    graphically generating a representation of at least a portion of the anatomical structure based on the geometric shapes.

2. The method of claim 1, wherein the coordinate system is a three-dimensional coordinate system.

3. The method of claim 1, wherein the anatomical structure is a heart.

4. The method of claim 1, wherein the geometric shapes comprise spheres.

5. The method of claim 1, wherein the geometric shapes comprise at least two different shapes.

6. The method of claim 1, wherein a size of each geometric shape is defined by a distance between the distal probe end and a surface of the anatomical structure.

7. The method of claim 1, wherein the geometric shapes originate from a plurality of points on the probe distal end.

8. The method of claim 1, further comprising transmitting ranging signals between the probe distal end and a reference point, wherein a position of each geometric shape within the coordinate system is determined based on the ranging signals.

9. The method of claim 6, further comprising transmitting a signal from the probe distal end, wherein the distance is determined based on an intersection between the signal and the surface of the anatomical structure.

10. The method of claim 9, wherein the signal is an ultrasound signal.

11. A medical system for use with an anatomical structure, comprising:
    an elongated medical probe including a shaft having a distal end and a signal emitting element carried by the shaft distal end;
    at least one processor configured for:
    generating data, based on signals emitted by the element, while the distal probe end is moved within the anatomical structure;
    defining a plurality of three-dimensional geometric shapes, based on the generated data, within a coordinate system; and
    graphically generating a representation of at least a portion of the anatomical structure based on the geometric shapes.

12. The system of claim 11, wherein the coordinate system is a three-dimensional coordinate system.

13. The system of claim 11, wherein the probe is an intravascular catheter.

14. The system of claim 11, wherein the geometric shapes comprise spheres.

15. The system of claim 11, wherein the geometric shapes comprise at least two different shapes.

16. The system of claim 11, wherein medical probe includes a plurality of signal emitting elements carried by the distal shaft end, and wherein the at least one processor is configured for defining the geometric shapes based on the signal emitted by each element.

17. The system of claim 11, wherein a size of each geometric shape is defined by a distance between the distal shaft end and a surface of the anatomical structure, and the at least one processor is configured for determining the distance based on an intersection between the emitted signal and the surface of the anatomical structure.

18. The system of claim 11, wherein the element is an ultrasound transducer.

19. The system of claim 11, further comprising:
    a tracking element carried by the distal shaft end; and
    ranging circuitry configured for transmitting signals between the tracking element and a reference point, wherein the at least one processor is configured for determining a position of each geometric shape within the coordinate system based on the signals.

20. The system of claim 11, further comprising an output device configured for displaying the graphical representation.

21. The system of claim 15, wherein the element is configured for emitting signals in at least two different modes, and the at least two different geometric shapes are respectively defined based on the at least two modes.

22. A method of graphically creating a representation of an anatomical structure, comprising:
    moving the distal end of an elongated probe within the anatomical structure;
    defining geometric shapes within a coordinate system while the distal probe end is moved within the anatomical structure, each of the geometric shapes originating from the distal probe end;
    determining a union of the geometric shapes; and
    graphically generating a representation of at least a portion of the anatomical structure based on the union of the geometric shapes.

23. The method of claim 22, wherein the coordinate system is a three-dimensional coordinate system.

24. The method of claim 22, wherein the anatomical structure is a heart.

25. The method of claim 22, wherein the geometric shapes comprise three-dimensional shapes.

26. The method of claim 22, wherein the geometric shapes comprise two-dimensional shapes.

27. The method of claim 22, wherein the geometric shapes comprise spheres.

28. The method of claim 22, wherein the geometric shapes comprise circles.

29. The method of claim 22, wherein the geometric shapes comprise at least two different shapes.

30. The method of claim 22, wherein a size of each geometric shape is defined by a distance between the distal probe end and a surface of the anatomical structure.

31. The method of claim 22, wherein the geometric shapes originate from a plurality of points on the probe distal end.

32. The method of claim 28, further comprising transmitting a signal from the probe distal end, wherein the distance is determined based on an intersection between the signal and the surface of the anatomical structure.

33. The method of claim 30, wherein the signal is an ultrasound signal.

34. The method of claim 22, further comprising transmitting ranging signals between the probe distal end and a reference point, wherein a position of each geometric shape within the coordinate system is determined based on the ranging signals.

35. A medical system for use with an anatomical structure, comprising:
    an elongated medical probe including a shaft having a distal end and a signal emitting element carried by the shaft distal end;
    at least one processor configured for:
    defining a plurality of geometric shapes within a coordinate system based on the signal emitted by the element;
    determining a union of the geometric shapes; and
    graphically generating a representation of at least a portion of the anatomical structure based on the union of the geometric shapes.

36. The system of claim 35, wherein the coordinate system is a three-dimensional coordinate system.

37. The system of claim 35, wherein the probe is an intravascular catheter.

38. The system of claim 35, wherein the geometric shapes comprise three-dimensional shapes.

39. The system of claim 35, wherein the geometric shapes comprise two-dimensional shapes.

40. The system of claim 35, wherein the geometric shapes comprise spheres.

41. The system of claim 35, wherein the geometric shapes comprise circles.

42. The system of claim 35, wherein the geometric shapes comprise at least two different shapes.

43. The system of claim 35, wherein medical probe includes a plurality of signal emitting elements carried by the distal shaft end, and wherein the at least one processor is configured for defining the geometric shapes based on the signal emitted by each element.

44. The system of claim 42, wherein the element is configured for emitting signals in at least two different modes, and the at least two different geometric shapes are respectively defined based on the at least two modes.

45. The system of claim 35, wherein a size of each geometric shape is defined by a distance between the distal shaft end and a surface of the anatomical structure, and the at least one processor is configured for determining the distance based on an intersection between the emitted signal and the surface of the anatomical structure.

46. The system of claim 35, wherein the element is an ultrasound transducer.

47. The system of claim 35, further comprising:
a tracking element carried by the distal shaft end; and
ranging circuitry configured for transmitting signals between the tracking element and a reference point, wherein the at least one processor is configured for determining a position of each geometric shape within the coordinate system based on the signals.

48. The system of claim 35, further comprising an output device configured for displaying the graphical representation.

49. The method of claim 1, wherein the graphical generation of the representation comprises creating a graphical anatomical shell around the geometric shapes.

50. The system of claim 11, wherein the graphical generation of the representation comprises creating a graphical anatomical shell around the geometric shapes.

51. The method of claim 22, wherein the graphical generation of the representation comprises creating a graphical anatomical shell around the union of the geometric shapes.

52. The system of claim 35, wherein the graphical generation of the representation comprises creating a graphical anatomical shell around the geometric shapes.

* * * * *

UNITED STATES PATENT AND TRADEMARK OFFICE
CERTIFICATE OF CORRECTION

PATENT NO. : 7,610,078 B2 Page 1 of 1
APPLICATION NO. : 11/213516
DATED : October 27, 2009
INVENTOR(S) : N. Parker Willis It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1097 days.

Signed and Sealed this

Twelfth Day of October, 2010

David J. Kappos
*Director of the United States Patent and Trademark Office*